United States Patent
Shen et al.

(10) Patent No.: US 9,764,048 B2
(45) Date of Patent: Sep. 19, 2017

(54) TARGETED MOLECULAR IMAGING PROBE AND METHOD FOR IN VIVO MOLECULAR IMAGING

(76) Inventors: Baozhong Shen, Harbin (CN); Zhen Cheng, Xiaogan (CN); Lihong Bu, Harbin (CN)

( * ) Notice: Subject to any disclaimer, the term of this patent is extended or adjusted under 35 U.S.C. 154(b) by 0 days.

(21) Appl. No.: 14/353,111

(22) PCT Filed: Jul. 30, 2012

(86) PCT No.: PCT/CN2012/079344
§ 371 (c)(1),
(2), (4) Date: Apr. 21, 2014

(87) PCT Pub. No.: WO2013/189113
PCT Pub. Date: Dec. 27, 2013

(65) Prior Publication Data
US 2015/0202335 A1    Jul. 23, 2015

(30) Foreign Application Priority Data
Jun. 18, 2012   (CN) .......................... 2012 1 0200690

(51) Int. Cl.
| | | |
|---|---|---|
| A61K 51/00 | (2006.01) | |
| A61M 36/14 | (2006.01) | |
| A61K 51/08 | (2006.01) | |
| A61K 49/00 | (2006.01) | |
| A61K 49/22 | (2006.01) | |

(52) U.S. Cl.
CPC ........ A61K 51/088 (2013.01); A61K 49/0002 (2013.01); A61K 49/0032 (2013.01); A61K 49/0056 (2013.01); A61K 49/223 (2013.01)

(58) Field of Classification Search
CPC ...... A61K 51/00; A61K 51/08; A61K 51/088; A61K 38/00; A61K 51/04; A61K 51/0497; A61K 31/00; A61K 39/00; A61K 2121/00; A61K 2123/00; A61K 49/223; A61K 49/0002; A61K 49/0032; A61K 49/0056; G01N 33/5011; C07K 7/06; C07K 7/08; C07K 14/47

USPC ........ 424/1.11, 1.65, 1.69, 9.1, 9.2, 9.3, 9.4, 424/9.5, 9.6; 530/300; 514/1, 1.1
See application file for complete search history.

(56) References Cited

FOREIGN PATENT DOCUMENTS

| | | |
|---|---|---|
| CN | 101678118 | 3/2010 |
| WO | WO 2009/010733 | 1/2009 |

OTHER PUBLICATIONS

Shibayama et al, Circ. Res., 2006, vol. 98, pp. 1365-1372.*
Baklaushev et al, Cell Technologices in Biology and Medicine, 209, No. 4, pp. 725-730.*
Kanaporis et al, Am. J. Physiol. Cell Physiol., Dec. 9, 2010, vol. 300, pp. C600-C609.*
Baklauhsev et al., "Immunofluorescent analysis of Connexin-43 using monoclonal antibodies to its extracellular domain," *Bulletin of Experimental Biology and Medicine*, 148(4):725-730, 2009, (Translated from Kletochune Technologii v Biologii i Medicine, No. 4, pp. 236-241, Dec. 2009)
Baklaushev et al., "Visualization of Connexin 43-positive cells of glioma and the periglioma zone by means of intravenously injected monoclonal antibodies," *Drug Delivery*, 18(5):331-337, 2011.
English translation of PCT International Search Report issued in International Patent Application No. PCT/CN2012/079344, dated Feb. 14, 2013.
Johnstone et al., "Enhanced connexin 43 expression delays intramitotic duration and cell cycle traverse independently of gap junction channel function," *Journal of Cellular Biochemistry*, 110(3):772-782, 2010.
Shibayama et al., "Identification of a novel peptide that interferes with the chemical regulation of connexin43," *Circulation Research*, 98:1365-1372, 2006.

* cited by examiner

*Primary Examiner* — D L Jones
(74) *Attorney, Agent, or Firm* — Parker Highlander PLLC

(57) ABSTRACT

Disclosed is a targeted molecular imaging probe consisting of a signal component, a component with a targeted affinity to Cx43 and a linker. The biochemical variation characteristic of connexin43 (Cx43) associated with cardiovascular diseases (especially arrhythmia) and neoplastic diseases can be reflected in the form of an image by using the targeted molecular imaging probe capable of being detected by an imaging device, to achieve in vivo molecular imaging.

10 Claims, 5 Drawing Sheets

Signaling component    Linker    Cx43 targeted affinity component    Imaging target Cx43 a    b c    d a b c a b c

SEQUENCE LISTING

<160> NUMBER OF SEQ ID NOS: 5

<210> SEQ ID NO 1
<211> LENGTH: 37
<212> TYPE: PRT
<213> ORGANISM: Artificial Sequence
<220> FEATURE:
<223> OTHER INFORMATION: Synthetic peptide

<400> SEQUENCE: 1

Asp Val Pro Gly Arg Asp Pro Gly Tyr Ile Lys Gly Gly Ser Ala
1               5                   10                  15

His Ala Arg Val Pro Phe Phe Ser His Ser Leu Asn Arg Asn Arg Lys
            20                  25                  30

Pro Ser Leu Tyr Gln
        35

<210> SEQ ID NO 2
<211> LENGTH: 37
<212> TYPE: PRT
<213> ORGANISM: Artificial Sequence
<220> FEATURE:
<223> OTHER INFORMATION: Synthetic peptide

<400> SEQUENCE: 2

Glu Ile Gln Pro Arg Ser Pro Leu Met Phe Ser Gly Gly Gly Ser Ala
1               5                   10                  15

His Ala Arg Val Pro Phe Phe Ser His Ser Ala Lys Glu Ala Arg Trp
            20                  25                  30

Pro Arg Ala His Arg
        35

<210> SEQ ID NO 3
<211> LENGTH: 37
<212> TYPE: PRT
<213> ORGANISM: Artificial Sequence
<220> FEATURE:
<223> OTHER INFORMATION: Synthetic peptide

<400> SEQUENCE: 3

Gly Ile Ala Ala Arg Glu Pro Asn Ser His Asp Gly Gly Gly Ser Ala
1               5                   10                  15

His Ala Arg Val Pro Phe Phe Ser His Ser Arg Asp Leu Trp Arg Lys
            20                  25                  30

Pro Ala Lys Ser Leu
        35

<210> SEQ ID NO 4
<211> LENGTH: 39
<212> TYPE: PRT
<213> ORGANISM: Artificial Sequence
<220> FEATURE:
<223> OTHER INFORMATION: Synthetic peptide

<400> SEQUENCE: 4

Trp Glu Glu Pro Arg Arg Pro Phe Thr Met Ser Gly Gly Gly Ser Ala
1               5                   10                  15

Glu Thr His Ala Arg Val Pro Phe Tyr Ser His Ser Pro Met Arg His
            20                  25                  30

Arg Leu Pro Gly Val His Leu
        35

```
<210> SEQ ID NO 5
<211> LENGTH: 34
<212> TYPE: PRT
<213> ORGANISM: Artificial Sequence
<220> FEATURE:
<223> OTHER INFORMATION: Synthetic peptide

<400> SEQUENCE: 5

Ser Asp Asp Leu Arg Ser Pro Gln Leu His Asn Gly Gly Gly Ser Ala
1               5                   10                  15

Val Pro Phe Tyr Ser His Ser His Met Val Arg Arg Lys Pro Arg Asn
            20                  25                  30

Pro Arg
```

TARGETED MOLECULAR IMAGING PROBE AND METHOD FOR IN VIVO MOLECULAR IMAGING

This application is a national stage application under 35 U.S.C. §371 of International. application No. PCT/CN2012/079344, filed Jul. 30, 2012, which claims the benefit of priority of China Patent Application No. 201210200690.6, filed with the Patent Office of China on Jun. 18, 2012, titled "TARGETED MOLECULAR IMAGING PROBE AND METHOD FOR IN VIVO MOLECULAR IMAGING". The entire contents of each of the above-referenced disclosures are specifically incorporated herein by reference.

The sequence listing that is contained in the file named "UNITP0004US_ST25.txt", which is 3 KB (as measured in Microsoft Windows®) and was created on Mar. 21, 2014, is filed herewith by electronic submission and is incorporated by reference herein.

FIELD OF THE INVENTION

The present invention relates to the field of medical technique, particularly to a Cx43 targeted molecular imaging probe and a process for in vivo molecular imaging.

BACKGROUND OF THE INVENTION

Gap junction remodeling is one of the common pathological bases involved in the onset and development of diseases such as arrhythmia, tumor, atherosclerosis, and the like, whereas connexin 43 (Cx43) is the basic structure unit constituting the gap junction as well as the main structure basis constituting gap junctions between myocardial cells. Cx43 is a type of connexin having a molecular weight of 43 Kd, the main role of which is to mediate the direct communication between adjacent cells. In heart, it mainly functions to form fast electrical impulses between cells, ensure the synchronism and harmony of the overall electrical activities in the heart, and maintain the electrical activities of myocardial cells and the synchronism of mechanical functions of contraction and relaxation. Consequently, the variation of Cx43 in terms of the amount, distribution, function, phosphorylation state, etc. (i.e., gap junction remodeling) will definitely result in electrical coupling dysfunction between myocardial cells, which mainly manifests as change of synchronism and harmony of electrical activities between cells, slowing down of electrical conduction, change of aeolotropy, etc. Various degrees of Cx43 gap junction remodeling occur in various adult acquired cardiovascular diseases, such as myocardial ischemia, arrhythmia, cardiac failure, hypertension, atherosclerosis, etc. Cx43 gap junction remodeling is an important structural basis for generation of various arrhythmia, especially reentrant tachycardia, and is also the primary cause for death and sudden death from various heart diseases.

Meanwhile, Cx43 is involved in various processes from growth to death in many cellular life cycles, directly mediates transmission of cellular growth regulatory signals between adjacent cells, and regulates cell growth, differentiation and apoptosis. The abnormity of Cx43 will directly result in abnormity of cellular growth regulation and disappearance of contact inhibition, terminal differentiation and apoptosis ability, which are manifested as extended or immortalized cell life cycle, and thereby leading to tumorigenesis.

Therefore, Cx43 has become a new research hotspot in the field of researches on cardiovascular diseases and tumor at home and abroad as a common molecule target for antiarrhythmic treatment and antitumor treatment. Many in vitro research methods are also developed accordingly for analysis of the amount and function (including phosphorylation state) of Cx43. These research methods include: applying PCR or RT-PCR to detect the expression of Cx43 at mRNA level; applying Western Blot to carry out semi-quantification studies on Cx43 proteins; observing subcellular level localization, gap junction remodeling, etc. of Cx43 through immunohistochemical and immunofluorescent staining techniques; analyzing the phosphorylation state of different phosphorylation sites of Cx43 by introducing specific antibodies of different phosphorylation sites of Cx43 and using matrix assisted laser desorption/ionization mass spectrometry, immobilized metal affinity chromatography, and LC-MS; using intercellular transfer assay of fluorescent dyes, introducing small molecular fluorescent dyes into cytoplasm through micro-injection method, in combination with fluorescence microscope technique, to assess the direct intercellular communication function mediated by Cx43 at cellular level; and the like. However, these in vitro detection processes mainly rely on analysis of vast results of experiments at cellular level or on ex vivo tissues.

Although in vitro detection processes can be used to judge and analyze Cx43 expression level and functional status of cells or tissues, all of them have certain limitations at the technical level:

(1) They require to obtain samples via cell culture, biopsy or autopsy, and therefore cannot be applied to human body directly;

(2) in vitro experimental results may not comply with the true situation in vivo: experimental conditions, devices and methods have great influence on in vitro tests, and some important ingredients in the sample may be lost during treatment thereof, leading to larger error, which makes the experimental results not comply with the true situation in vivo;

(3) in vitro experiments go against dynamic studies: in vitro experiments require to execute experimental animals at different time points to acquire tissues or obtain materials through repeated biopsies, can only be used to observe certain stage of a disease, cannot achieve the actual dynamic research in the same animal, and are difficult to come into an accurate conclusion on the whole process of such a complex, progressive disease;

(4) Their operations are complicated, time-consuming and costly, and are substantially stochastic. Consequently, in vivo visual research of Cx43 can provide a new idea for solving these problems, whereas the appearance of molecular imaging technology makes it become possible.

Molecular imaging is a subject for carrying out imaging, qualitative and quantitative researches on biological processes in living human and animal body at cellular and molecular levels through imaging methods. It is notably characterized by application of a molecular probe, and employs multiple imaging means to image specific target in vivo. Imaging means include radionuclide imaging, magnetic resonance imaging (MRI), magnetic resonance spectroscopy (MR spectroscopy, MRS), optical imaging (OI), ultrasound imaging (US) and integration of multi-mode imaging, etc. By means of these imaging techniques, certain specific physiological or pathological processes in a life system, such as gene expression, interaction between proteins, signal transduction, metabolism of cells, cell tracking, etc., can become visual in the form of images.

In the Cx43 visualization protocol performed by V Baklaushev et al., a probe is synthesized using the specific antibody of Cx43 protein extracellular E2 segment as a targeted affinity component, and using radioactive isotope 125I and fluorescent dye Alexa660 as signal components. a γ-ray counter and a fluorescence microscope are utilized to detect the abnormal expression of Cx43 in brain glioma, but still failing to get rid of the limitations of in vitro detection methods:

(1) $^{125}$I is not a nuclein suitable for in vivo imaging, only the γ-ray counter can be used for detection, and the test results are not visual enough. Therefore, in the study, after intravenous injection of the probe $^{125}$I-MAbE2Cx43, the animals were sacrificed and tissues were acquired, and a γ-ray counter was employed to carry out radioactivity analysis;

(2) Alexa660 is also not a fluorescent dye suitable for in vivo imaging, can only be used in an immunohistochemical staining analysis, and therefore, in the study, after intravenous injection of the probe Alexa660-MAbE2Cx43, the animals were sacrificed and tissues were acquired and produced into a frozen section, and a fluorescence microscope was employed to analyze the tissues;

(3) the MAbE2Cx43 antibody used as the affinity component is expensive, can induce immunogenic response, and thereby induce side effects. What's more, due to the larger molecular weight of the antibody, the non-specific absorption will be higher, and it is difficult to obtain ideal pharmacokinetic characteristics and biological distribution characteristics after injection into the body, which renders the detection results inaccurate, and the method inconvenient to apply. Currently, there exists an urgent need for a process for in vivo detection and quantification of Cx43.

SUMMARY OF THE INVENTION

The technical problem mainly solved by the present invention is the in vivo detection and quantification of Cx43. Through carrying out in vivo detection and quantification of Cx43 by means of an in vivo molecular imaging technique, expression quantity, distribution, and function of Cx43 in vivo as well as dynamic change situation of Cx43 during the development of a disease can be determined, the optimum timing and dose of targeted therapy intervention with Cx43 can be determined, and accurate and objective evaluation of the therapeutic effect of "reconstruction of Cx43" therapy can be carried out, so as to achieve fast prognostic assessment of a disease such as reentrant arrhythmias, malignant tumor, etc., and the monitoring of the therapeutic effect of Cx43 targeted therapy.

In one aspect, the present invention provides a process for in vivo molecular imaging, said process comprises:

providing a Cx43 targeted molecular probe consisting of three components: a signaling component, a targeted affinity component and a linker, wherein the signaling component is a moiety which is detectable by an imaging device, the targeted affinity component is a moiety which specifically binds to Cx43, and the linker links the signaling component to the targeted affinity component;

carrying out optical imaging, positron emission tomography, single photon emission tomography, magnetic resonance imaging, photoacoustic imaging, ultrasonic imaging or other integrated imaging techniques for in vivo imaging preferably PET/CT and PET/MRI, to the site to be detected in a patient by using the Cx43 targeted molecular probe.

Preferably, the targeted affinity component specifically binds to the carboxyl terminal of the Cx43.

More preferably, the targeted affinity component is selected from the group consisting of:
I. Cx43SP1, Gly-Ala-Pro-Gly-4 Hyp-Pro-Tyr
II. Cx43SP2, Gly-D-Tyr-D-Pro-D-Hyp-Gly-D-Ala-Gly
III. Cx43SP3, which has the following structural formula:

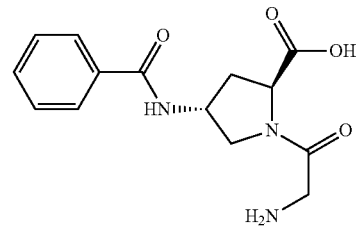

IV. Cx43SP4, which comprises 5 analogs having a structure of RXP-X, specifically:
RXP-A, having the amino acid sequence of SEQ ID No.1;
RXP-B, having the amino acid sequence of SEQ ID No.2;
RXP-C, having the amino acid sequence of SEQ ID No.3;
RXP-D, having the amino acid sequence of SEQ ID No.4;
RXP-E, having the amino acid sequence of SEQ ID No.5.

Preferably, the signaling component is one or more selected from the group consisting of radioisotope, fluorescent dye, quantum dot, paramagnetic material, magnetic nanoparticle, super-paramagnetic material, ultrasound microbubble, and photoacoustic nanoparticle.

Preferably, the linker is a chelating agent selected from the group consisting of DTPA, DOTA, DOTAGA, NOTA, NODAGA, TETA, CB-TE2A, Sar, NODA, and the like, or other chemical means capable of directly linking the signaling component to Cx43 targeted affinity component.

In another aspect, the present invention provides a targeted molecular probe consisting of three components: a signaling component, a targeted affinity component and a linker linking the signaling component to the targeted affinity component, wherein the signaling component is a moiety which is detectable by an imaging device, the targeted affinity component is a moiety which specifically binds to Cx43, and the linker links the signaling component to the targeted affinity component.

Preferably, the targeted affinity component in the targeted molecular probe specifically binds to the carboxyl terminal of the Cx43.

More preferably, the targeted affinity component is selected from the group consisting of:
I. Cx43SP1, Gly-Ala-Pro-Gly-4 Hyp-Pro-Tyr
II. Cx43SP2, Gly-D-Tyr-D-Pro-D-Hyp-Gly-D-Ala-Gly
III. Cx43SP3, which has the following structure:

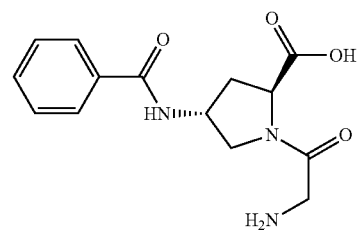 [SMILES: NCC(=O)N1C[C@H](NC(=O)c2ccccc2)C[C@H]1C(=O)O]

IV Cx43SP4, which comprises 5 analogs having a structure of RXP-X, which has the following sequence:

| RXP-X | Sequences | SEQ ID NO: |
|---|---|---|
| RXP-A | DVPGRDPGYIKGGGSAHARVPFFSHSLNRNRKPSLYQ | 1 |
| RXP-B | EIQPRSPLMFSGGGSAHARVPFFSHSAKEARWPRAHR | 2 |
| RXP-C | GIAAREPNSHDGGGSAHARVPFFSHSRDLWRKPAKSL | 3 |
| RXP-D | WEEPRRPFTMSGGGSAETHARVPFYSHSPMRHRLPGVHL | 4 |
| RXP-E | SDDLRSPQLHNGGGSAVPFYSHSHMVRRKPRNPR | 5 |

Preferably, the signaling component is one or more selected from the group consisting of radioisotope, fluorescent dye, quantum dot, paramagnetic material, magnetic nanoparticle, super-paramagnetic material, ultrasound microbubble, and photoacoustic nanoparticle.

Preferably, the linker is a chelating agent selected from the group consisting of DTPA, DOTA, DOTAGA, NOTA, NODAGA, TETA, CB-TE2A, Sar, NODA, and the like, or direct linkage of the signaling component and the Cx43 affinity component by means of other direct chemical reactions.

Molecular probe: a labeled compound molecule capable of target-specifically binding to a particular biological molecule (such as a protein, DNA, and RNA) or a cell structure, and is available for in vivo or (and) in vitro imaging tracing, it can reflect the amount and (or) function of its target biological molecule in vivo and (or) ex vivo. It can be simply understood as a diagnostic agent for molecular imaging.

A molecular imaging probe must have the following 2 important features: (1) it has high affinity and target specificity for target molecule which is highly associated with a disease; (2) it is available for in vitro tracing by an imaging device. A probe is mainly used for imaging, quantification and measurement of biological processes in vivo. Its basic structure generally comprises three portions: a signaling component, an affinity component and a linker. A signaling component refers to a contrast agent or marker portion (such as radionuclide, fluorescein, paramagnetic atom, ultrasound microbubble, etc.) which can generate imaging signals and can be detected by an imaging technique with high precision. An affinity component is a targeted molecule, i.e., a moiety specifically binding to imaging targets, such as a ligand or an antibody, etc. The signaling component and the affinity component can be directly linked via a radiochemical technique or a chemical technique for linking biological molecules, and can also be linked via a linker, namely, introducing crosslinking or derivatizing reagents.

The present invention provides a Cx43 molecule targeted specific probe, which is formed by labeling a Cx43 target specific binding polypeptide via an imaging method such as radioisotope, fluorescent dye, quantum dot, nanoparticle, magnetic material, ultrasound microbubble, photoacoustic imaging material, multi-mode imaging, etc. Through introducing this type of probe and applying imaging means such as positron emission tomography (PET), single photon emission tomography (SPECT), optical imaging, ultrasonic imaging, magnetic resonance imaging, photoacoustic imaging, multi-mode imaging, etc., the amount, distribution and function of Cx43 in the area of interest can be detected under normal physiological and pathological situations in vivo, and the change characteristics of Cx43 at different stages during progress of a disease.

It has been proven upon research that the probe has good stability in vivo, high Cx43 target molecular imaging specificity, high accuracy, good image contrast, and is suitable for diagnosing cardiovascular diseases (especially arrhythmia) and tumor, monitoring therapeutic effect of Cx43 targeted therapy, determining the optimum timing and dose for targeted therapy intervention, and conducting accurate and objective evaluation on the therapeutic effect of "reconstitution of Cx43" therapy. Meanwhile, the probe also provides an effective process for basic research on tumor and cardiovascular diseases, and provides a new means for studying the correlation between Cx43 and the characteristics in occurrence and development of a disease.

The present invention further provides an imaging composition, which comprises the above-mentioned targeted molecular probes.

The present invention further provides a use of the targeted molecular probe in the preparation of a reagent for diagnosing a disease associated with abnormal Cx43 expression.

Preferably, the disease associated with abnormal Cx43 expression is a disease molecularly characterized by abnormal expression or function of Cx43, and mainly includes arrhythmia or tumor.

The present invention establishes a noninvasive and visual Cx43 in vivo molecular imaging process, synthesizes a probe detectable by means of an imaging device, visually shows the distribution and amount of Cx43, and preliminarily evaluates the function thereof.

This technique is safe to establish, noninvasive, in vivo, dynamic, visual, accurate, and can be applied to human body directly.

The diagnostic agent (molecular probe) for Cx43 targeted imaging developed in the present invention has good pharmacokinetic characteristics and biological distribution characteristics, gives more accurate test results, can be applied more conveniently, and visually reflects biochemical features of a disease such as arrhythmia and tumor in the form of image.

The targeted specific probe of the present invention has the following advantages:

1). It has Cx43 Target Specificity to Assure the Accuracy of the Targeted Detection of Cx43 Molecular Imaging Non-specific probes used in conventional imaging and nuclear medical examinations cannot specifically recognize and bind to biological molecules in vivo, and therefore can only provide downstream information on molecular changes (anatomic, pathological and physiological changes) in a disease, or information on the overall morphology and function of a disease, such as the changes of blood flow volume and blood perfusion. In order to accurately detect key marker molecules during the development of a disease, the probe is required to be able to specifically recognize and bind to an in vivo molecular marker, provide information on a disease at molecular level, and deepen the understanding of biological processes of a disease. In addition, by means of the targeted specific probe, the nonspecific binding of the probe to other non-imaging targets may be effectively reduced, which is more helpful in accurate quantification of the imaging target.

2). In Vivo Visualization of Cx43 can Assure Safety, Noninvasiveness and Visuality of Cx43 Molecular Imaging Detection In order to achieve the in vivo visualization of key molecular markers during the development of a disease, the probe should have the property of emitting imaging signal for a noninvasive imaging device to detect in vitro so as to visually show the distribution of the molecular marker via image. This is because that the imaging detection is safe, noninvasive and visual.

3). Molecular Probes have High Affinity with Target Cx43

The premise of achieving Cx43 in vivo detection and obtaining an ideal molecular imaging image is aggregation of the molecular probe with high concentration at the imaging target. In other words, the probe should bind to target spots at earlier stage after it arrives at the target area, and dissociate relatively late, so as to make sure that the probe achieves ideal aggregation status at the target after several blood circulation cycles.

4). High Sensibility of Molecular Probe in Detection of Cx43

In order to detect the change of molecular markers at the early stage of a disease or early stage of therapeutic intervention, the probe is generally required to be able to detect a very small amount of biological markers, namely, to have high sensibility. In addition, unlike therapeutic pharmaceuticals, an ideal molecular probe has to make sure that it generates minimum biological influences or pharmacological effects. Therefore, the probe is required to have sufficiently high sensibility, such that only small amount of the probe is needed to acquire an ideal image, thereby minimizing the amount of the probe introduced into the body, and reducing the pharmacological effects induced by the probe.

5). High Contrast of Cx43 In Vivo Molecular Imaging

An image with high contrast requires sufficiently high signal intensity of the diseased area, namely very high target/background ratio and signal/noise ratio. This requires that the probe has ideal biological distribution features, i.e., the probe aggregates in the target area in a large amount and stays for a long time, but has a low uptake rate and rapid clearance rate in normal tissues and organs.

6). In Vivo Stability of the Molecular Probe

Although the amount of the molecular probe introduced may be very low, maintaining the stability and integrity of the molecular probe in vivo is still a challenge, as many enzymes capable of degrading the probe are present in plasma or target tissue. The quality of the image and the accuracy of the quantitative research depend on the stability of the probe in vivo.

7). Low Immunogenicity and Toxicity of the Molecular Probe

The molecular probe applied to the human body must be safe, without any immunogenicity and toxicity. The pharmacological effects generated should be minimal.

8). Easy Production of the Molecular Probe and Low Cost

The molecular probe is easy to produce, and the cost thereof is low, which is helpful for wide clinical applications. If the production process is complicated and the cost is high, the clinical transformation of the molecular probe will definitely be affected.

a: HeLa-Cx43 cells uptake a large amount of the probe Cy5.5-Cx43SP (green) after co-incubation of Cy5.5-Cx43SP with HeLa-Cx43 cells;

b: Cy5.5-Cx43SP is not uptaken by HeLa cells in the control group after co-incubation of Cy5.5-Cx43SP with HeLa cells;

c: after previous blocking by introduction of excess unlabeled Cx43SP, and subsequent co-incubation of Cy5.5-Cx43SP with HeLa-Cx43 cells, the amount of Cy5.5-Cx43SP uptaken by HeLa-Cx43 cells decreases significantly, with almost no Cy5.5-Cx43SP being uptaken;

d: after blocking by introduction of excess unlabeled Cx43SP and subsequent co-incubation of Cy5.5-Cx43SP with HeLa cells, the HeLa cells still do not uptake Cy5.5-Cx43SP. The probe is proven to have good target specificity.

Figure 3:
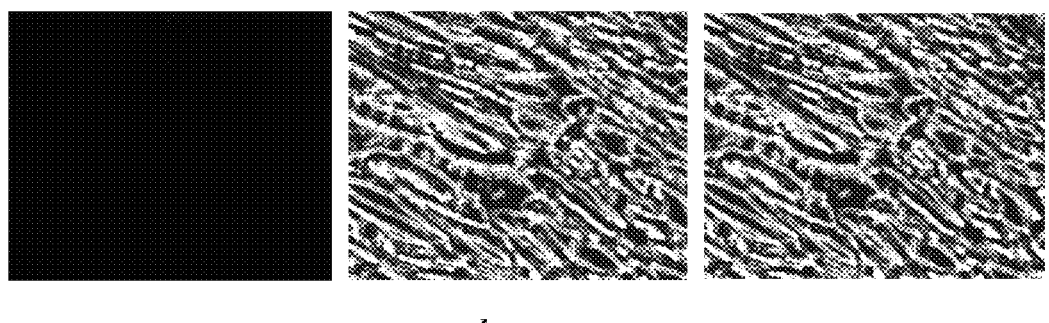

FIG. 3 shows fluorescent micrographs of frozen sections of tissues using muscles as the control:

a: 1 h after tail vein injection of Cy5.5-Cx43SP, the fluorescent micrograph of a frozen section of muscle, showing that Cy5.5-Cx43SP was not gathered in the muscular tissue;

b: the bright field picture of the frozen section of muscle, showing the morphology of the muscular tissue;

c: merged picture of the frozen section of muscle and the fluorescent micrograph.

Figure 4:
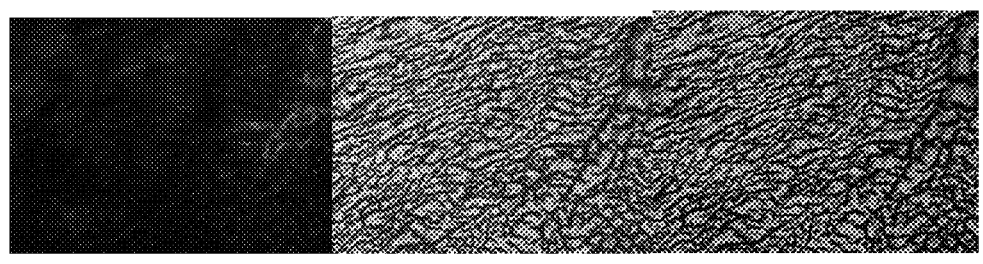

FIG. 4 is a fluorescent micrograph of a frozen section of heart tissue after in vivo injection of the probe:

a: 1 h after tail vein injection of Cy5.5-Cx43SP, the fluorescent micrograph of a frozen section of myocardium, showing that Cy5.5-Cx43SP is gathered in the myocardial tissue in large amount;

b: 1 h after tail vein injection of Cy5.5-Cx43SP, the bright field picture of the frozen section of myocardium, showing the morphology of the myocardial tissue;

c: 1 h after tail vein injection of Cy5.5-Cx43SP, a merged photograph of the frozen section of myocardium and the fluorescent micrograph, showing that Cy5.5-Cx43SP is gathered in the myocardial tissue in large amount, and is mainly distributed at the location of gap junctions between myocardial cells.

Figure 5:
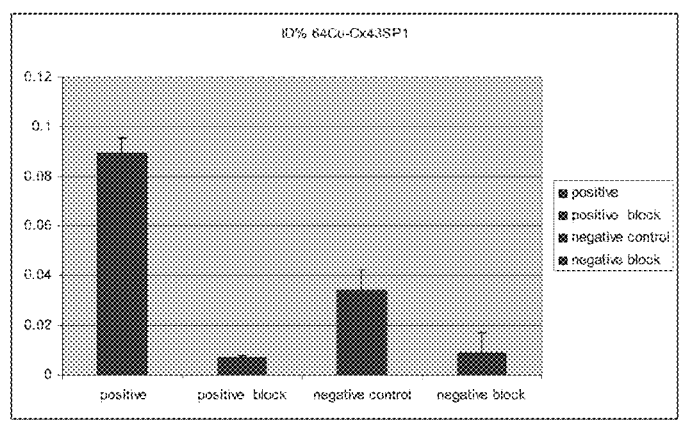

FIG. 5 shows the binding and blocking experiments of $^{64}$Cu-NODA-Cx43SP1 with HeLa-Cx43 cells.

Figure 6:
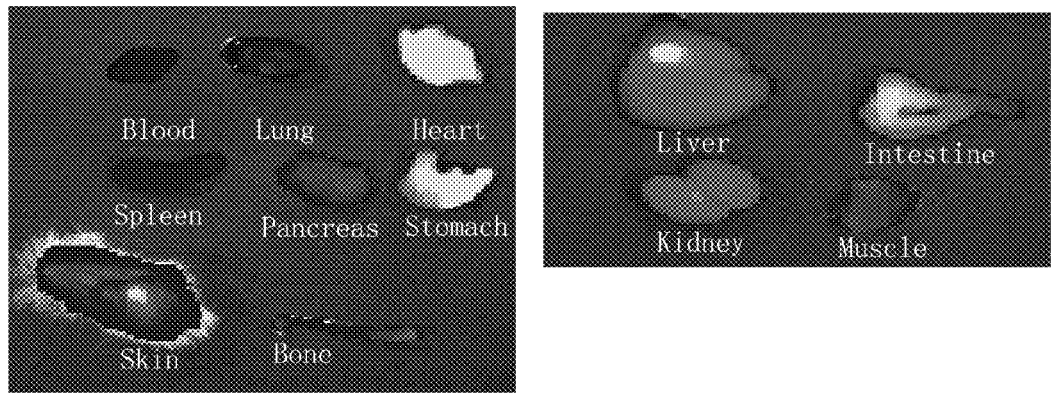

FIG. 6 are near-infrared fluorescence images of ex vivo main tissues and organs: 1 h after tail vein injection of the probe Cy5.5-Cx43SP into a mouse, the probe is significantly gathered in the heart, stomach, liver, gall bladder and intestinal tract, and mostly excreted via liver and intestinal tract.

Figure 7:
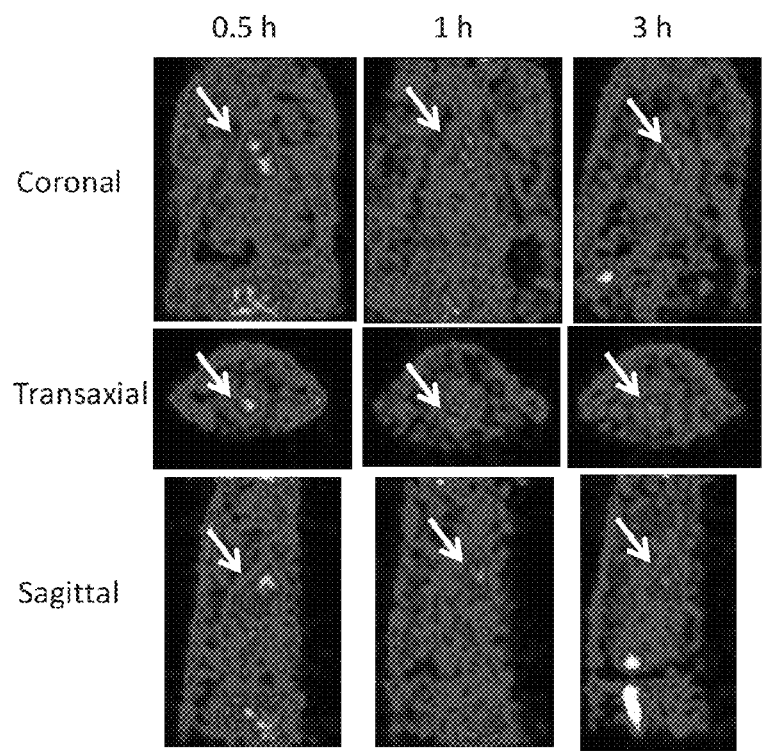

FIG. 7 shows PET images of $^{64}$Cu-NOTA-Cx43SP1 in a normal rat at different times, showing that the probe is significantly gathered in the heart. The injection amount of $^{64}$Cu-NOTA-Cx43SP1 is about 200 microcurie.

Figure 8:
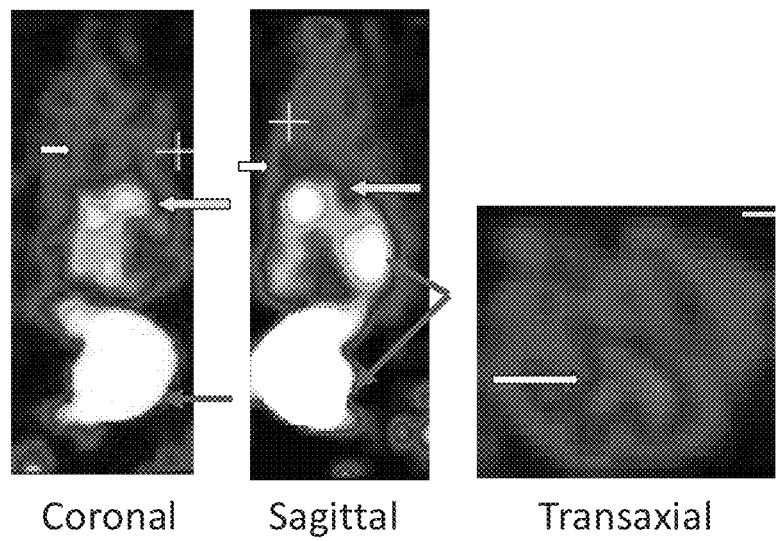

FIG. 8 shows PET images of $^{64}$Cu-NOTA-Cx43SP1 in a normal mouse at 1 h, showing that the probe is significantly gathered in the heart. The injection amount of $^{64}$Cu-NOTA-Cx43SP1 is about 50 microcurie.

Figure 9:
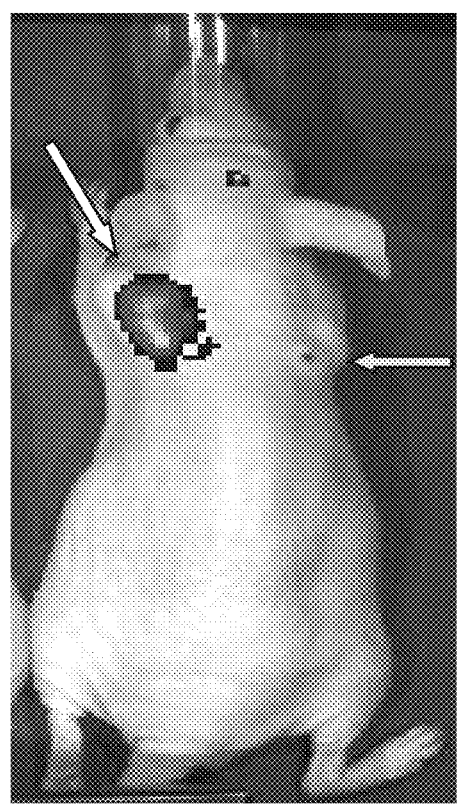

FIG. 9: near-infrared imaging experiment of a tumor in a living mouse: 1 h after tail vein injection of the probe Cy5.5-Cx43SP1 into a mouse, the probe is gathered at tumor site of HeLa-Cx43 overexpressing Cx43 in large amount, and is not concentrated at the HeLa tumor site in the control group on the right side.

Figure 10:
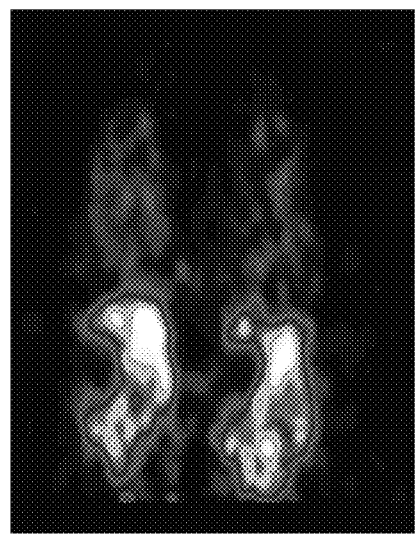

FIG. 10: PET imaging experiment of tumor in a mouse in vivo: 1 h after tail vein injection of the probe $^{64}$Cu-NODA-Cx43SP1 into a mouse, the probe is gathered at tumor site of HeLa-Cx43 overexpressing Cx43 in large amount (on the left side).

DETAILED EMBODIMENTS

The present invention discloses a Cx43 targeted molecular imaging probe and a process for molecular imaging in vivo, which can be achieved by a person skilled in the art in light of the present disclosure through appropriately improving process parameters. It should be particularly noted that, all similar substitutions and modifications would be obvious for a person skilled in the art, and should be construed as being included in the present invention. The process and use of the present invention have been described with reference to preferable examples, and those skilled in the art can make modifications or proper alterations or combinations to the process and use as described herein without departing from the contents, spirit and scope of the present invention, in order to achieve and apply the technology of the present invention.

In order for those skilled in the art to better understand the technical solutions of the present invention, the present invention will be further illustrated in detail in combination with specific examples.

EXAMPLE 1

Cx43 Targeted Affinity Component—Cx43 Targeted Binding Peptides (Cx43SP)

Any of the following 4 types of polypeptides (Cx43 targeted binding peptides) can specifically bind to the carboxyl terminal of Cx43, and therefore can be used to synthesize Cx43 targeted molecular probe.

1) Structure of Cx43SP1:

Gly-Ala-Pro-Gly-4 Hyp-Pro-Tyr, also called: AAP10, molecular formula: $C_{26}H_{37}N_7O_8$, molecular weight: 575.6, the structure thereof is as shown below:

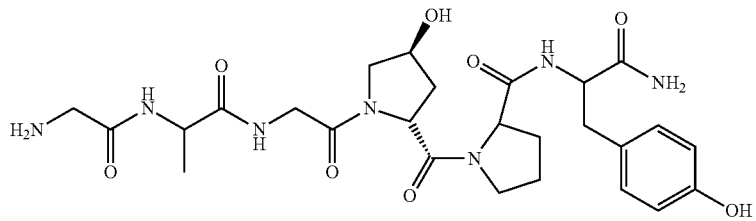

Cx43SP1 is the most important targeted affinity component in the molecular probes of the present invention, and is a polypeptide which can specifically recognize and bind to Cx43 in vivo, and consists of 6 amino acids. Cx43SP1 comprises a series of antiarrhythmic polypeptides extracted by Aonuma S et al. in 1980 from the atrial tissue of a cattle, which functions via action on Cx43, and therefore has been named antiarrhythmic peptide10 (AAP10). However, as the structures of AAP10 are not stable in plasma, they have no further clinical applications. The present inventors carried out chemical modifications to the structures of AAP10, and synthesized a probe for Cx43 in vivo imaging, which has been verified to have ideal in vivo stability. Since in the present invention, the chemical structure is no longer used as an antiarrhythmic agent, but as a targeted affinity component of a Cx43 targeted molecular imaging probe, it is named Cx43 Specific Peptide 1. The hippocrepiform domain of Cx43SP1 can specifically bind to the receptor domain of the carboxyl terminal of Cx43.

2) The Structure of Cx43SP2:

Gly-D-Tyr-D-Pro-D-Hyp-Gly-D-Ala-Gly, the structure thereof is as shown below:

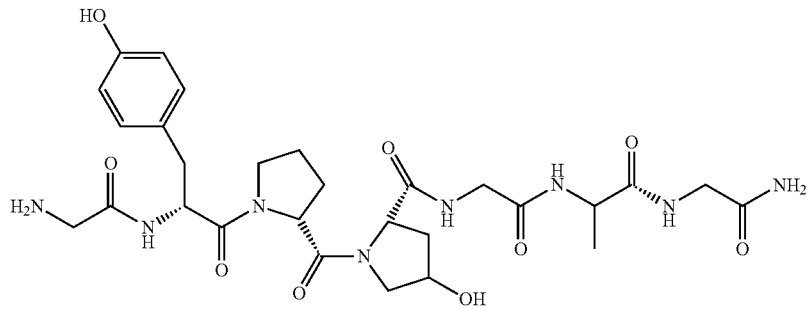

Cx43SP2 is an analog of Cx43SP1, in which some L form amino acids in Cx43SP are substituted with D form amino acids, so as to increase stability. Cx43SP2 is now on the stage of clinical trial as an antiarrhythmic agent. The trade name of Cx43SP2 is rotigaptide, also called CHEMBL450656, GAP-486, ZP123. Formula: $C_{28}H_{39}N_7O_9$, molecular weight: 617.65076.

3) The Structure of Cx43SP3:

Cx43SP3 is a functional analog of Cx43SP2, also called GAP 134, with a molecular weight of 291.3, and the structure thereof is as shown below:

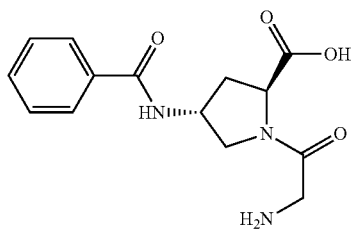

4) As Shown in Table 1, Cx43SP4 Comprises 5 Types of Amino Acid Sequences Containing the Characteristic Structure of RXP-E:

TABLE 1

Amino acid sequences of Cx43SP4

| RXP-X | Sequences | SEQ ID NO: |
|---|---|---|
| RXP-A | DVPGRDPGYIKGGGSAHARVPFFSHSLN RNRKPSLYQ | 1 |
| RXP-B | EIQPRSPLMFSGGGSAHARVPFFSHSAK EARWPRAHR | 2 |
| RXP-C | GIAAREPNSHDGGGSAHARVPFFSHSRD LWRKPAKSL | 3 |
| RXP-D | WEEPRRPFTMSGGGSAETHARVPFYSHS PMRHRLPGVHL | 4 |
| RXP-E | SDDLRSPQLHNGGGSAVPFYSHSHMVRR KPRNPR | 5 |

Cx43SP3 is a type of polypeptides screened by Mario Delmar et al. in 2006 through phage display technique, which can specifically bind to carboxyl terminal (amino acids 255-382) of Cx43 and are comprised of 34 amino acids. Their basic binding motif is RXP-X, and thus also called RXP series of polypeptides. They are proposed to be used in antiarrhythmic therapy. Wherein, RXP-E has more potential applications than the other polypeptides.

EXAMPLE 2

Preparation of Cx43 Targeted Molecular Probes

Figure 1:
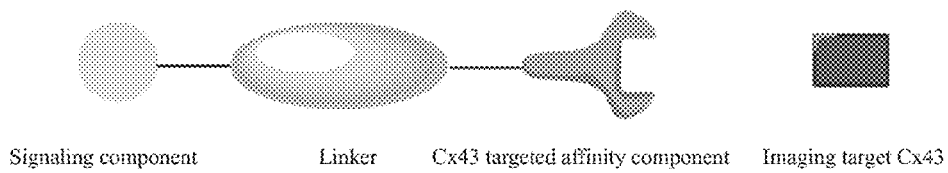
FIG. 1 is a schematic diagram of the structure of Cx43 targeted molecular imaging probe.

The general formula of Cx43 targeted molecular probe of the present invention is as shown in FIG. 1.

(1) The imaging target is Connexin 43 (Cx43), the carboxyl terminal (C-terminal) of Cx43 has a gating particulate structure, which is functionally equivalent to specific receptor domain, is the main binding target of Cx43SP, and is the target of Cx43 targeted imaging of the present invention.

(2) Signaling component: a moiety in the probe detectable with an imaging device, and in the present patent it is mainly an radioisotope (PET and SPECT imaging), a fluorescent dye and a quantum dot (optical imaging), a paramagnetic material, a super-paramagnetic material and magnetic nanoparticles (magnetic resonance imaging), ultrasound microbubbles (ultrasonic imaging), various photoacoustic nanoparticles (photoacoustic imaging) and an imaging material formed by a combination of the various components as mentioned above for detection by means of a multi-mode imaging technique.

(3) Targeted affinity component: a moiety in the probe specifically binding to the imaging molecular target, the binding therebetween has high specificity and high affinity, like the relationship between "a key and a lock". The present invention mainly involves polypeptides and small molecular structures in example 1.

(4) Linker: a moiety linking the signaling component to the targeted affinity component. Alternatively, the linker may not be introduced, and the signaling component is directly linked to the Cx43 affinity component via employing a chemical method.

EXAMPLE 3

Preparation of Radioisotope Labeled Cx43 Targeted Molecule Probe

Each of the 4 types of polypeptides in example 1 can specifically bind to the carboxyl terminal of Cx43, and therefore can be used to prepare the labeled Cx43 targeted molecular probe. In the examples illustrating the synthesizing processes as follows, Cx43SP1 is used as a representative polypeptide.

The signaling component is a positron emission radioisotope or a single photon radionuclide, which can be used in positron emission tomography (PET) or single photon emission tomography (SPECT) clinically or for a small animal. Through selecting a proper linker or employing a radioactive chemical method, the radioisotope can bind to targeted polypeptides. The linker employed is also called a bifunctional chelating agent. The bifunctional chelating agent possesses not only a functional motif group, but also a group binding to Cx43SP, so as to link the above two components to form a Cx43 targeted molecular probe.

Divalent ($M^{2+}$) or Trivalent Metal Ion ($M^{3+}$) Labeled Cx43SP

Depending on different properties of radionuclides, different linkers can be selected.

For details, please refer to Table 2.

TABLE 2

Commonly used radioisotopes, bifunctional chelating agents and thus synthesized Cx43 targeted probe

| Radionuclides | Linker | Linker modified Cx43SP |
|---|---|---|
| ¹¹¹In | DTPA, ca-DTPA, Ibca-DTPA, lys-DTPA, CHX-A″-DTPA | DTPA-R, SCN-CHX-A″-DTPA |

TABLE 2-continued

Commonly used radioisotopes, bifunctional chelating agents and thus synthesized Cx43 targeted probe

| Radionuclides | Linker | Linker modified Cx43SP |
|---|---|---|
| | Vinyl-DTPA | |
| | glu-DTPA | |
| $^{111}$In $^{86/90}$Y $^{177}$Lu $^{67/68}$Ga $^{212}$Pb $^{212}$Bi/$^{213}$Bi $^{89}$Zr $^{225}$Ac | DOTA | DOTA-R |
| | C-DOTA | DOTAGA-R |
| | PA-DOTA | |
| | DODASA | |

TABLE 2-continued
Commonly used radioisotopes, bifunctional chelating agents and thus synthesized Cx43 targeted probe
| Radionuclides | Linker | Linker modified Cx43SP |
|---|---|---|
| | 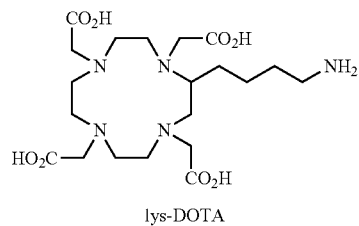<br>lys-DOTA | |
| $^{67/68}$Ga<br>$^{111}$In<br>$^{64/67}$Cu<br>$^{203}$Pb<br>$^{212}$Pb | 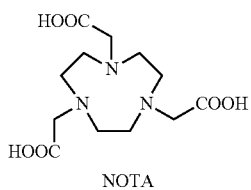<br>NOTA | 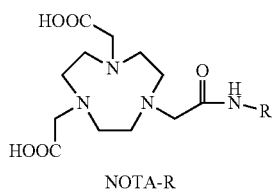<br>NOTA-R |
| | 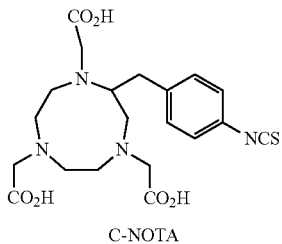<br>C-NOTA | 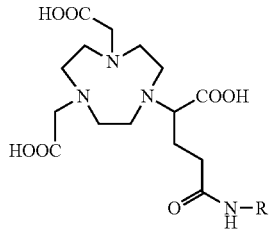<br>NODAGA-R |
| | 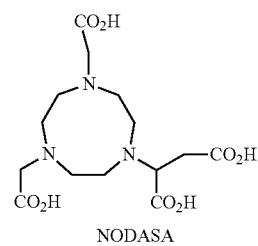<br>NODASA | 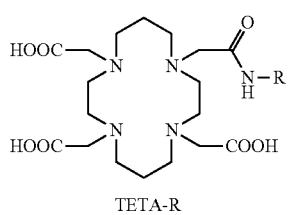<br>TETA-R |
| | 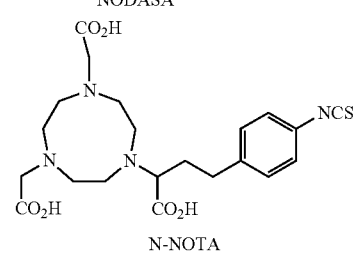<br>N-NOTA | |

TABLE 2-continued

Commonly used radioisotopes, bifunctional chelating agents and thus synthesized Cx43 targeted probe

| Radionuclides | Linker | Linker modified Cx43SP |
|---|---|---|
| | TCMC | |
| | TETA | |
| | 2C-TETA | |
| | NC-TETA | |
| | BF-PEPA | |
| | BF-HEHA | |

TABLE 2-continued

Commonly used radioisotopes, bifunctional chelating agents and thus synthesized Cx43 targeted probe

| Radionuclides | Linker | Linker modified Cx43SP |
|---|---|---|
| $^{64/67}$Cu | CB-TE2A | CB-TE2A-R |
| | Sar | SarAr-R |
| | NODA | AmBaSar-R |

Note:
R is Cx43SP.
DTPA: diethylene triamine pentaacetic acid
DOTA: 1,4,7,10-tetraazacyclododecane-1,4,7,10-tetraacetic acid
DOTAGA: 1-(1-carboxy-3-carboxypropyl)-1,4,7,10-tetraazacyclododecane-1,4,7,10-triacetic acid
NOTA: 1,4,7-triazacyclononane-1,4,7-triacetic acid
NODAGA : NOTA subjected to functional modification by a glutaric acid arm 2-(p-SCN-Bz)-NOTA: NOTA subjected to functional modification by a benzyl isothiocyanate
TETA: 1,4,8,11-tetraazacyclotetradecane-1,4,8,11,tetraacetic acid
CB-TE2A : Attachment of two carboxymethyl pendant arms to cross-bridged (CB)-cyclam leads to CB-TE2A
Sar: sarcophagine (3,6,10,13,16,19-hexa azabicyclo [6.6.6] icosane)
SarAr and AmBa Sarare carboxy are respectively carboxylic acid and amino derivatives of Sar
NODA: sodium 1,4,7-triazacyclononane-1,4-diacetate Many radioisotopes and bifunctional chelating agents are mentioned above. Therefore, $^{64\ Cu\ labeled\ Cx}$43SP is taken as an example here to illustrate the process for labeling Cx43SP with divalent ($M^{2+}$) or trivalent metal ions ($M^{3+}$) of a radioisotope.

Modifying Cx43SP with NODA: Into an excess of NODA were added appropriate amount of N,N-dimetbylformamide (DMF) and 2% of N,N-diisopropyl ethylamine (DIPEA), and the mixture was vibrated overnight at room temperature. After isolation and purification on high performance liquid chromatography (HPLC), the products thus obtained were analyzed and identified via mass spectrometry. The chemical reaction formula of modifying Cx43SP1 with NODA is as follows:

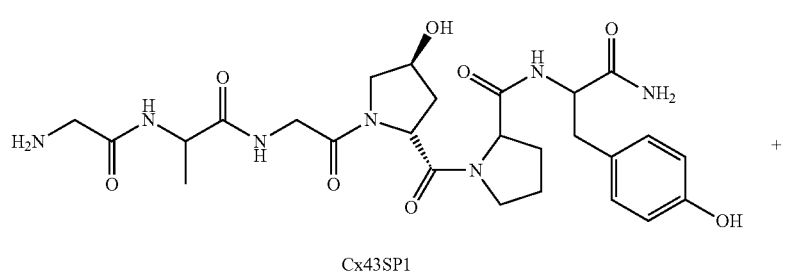

Cx43SP1

+

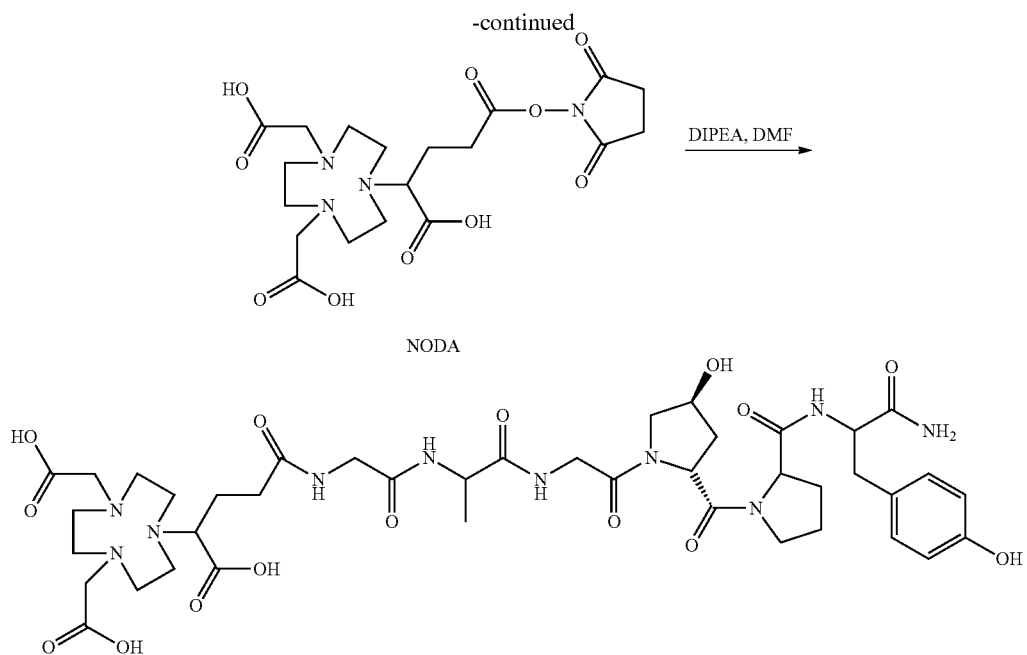

NODA

The Chemical Reaction Formula of Modifying Cx43SP1 with NODA $^{64}$Cu labeling: 10 μg of Cx43SP-NODA was dissolved in 200 μl of ammonium acetate buffer with pH of between 4 and 5, and then 50 μL of $^{64}$CuCl$_2$ (pH between 5 and 6). The mixture was reacted at 37° C. for 1 hour. The radiolabeled product was isolated and purified with radioactive detector—high performance liquid chromatography (RP-HPLC), and the labeling rate, radiochemical purity, and specific activity were tested. The chemical reaction formula of labeling NODA-Cx43SP1 with $^{64}$Cu is as follows:

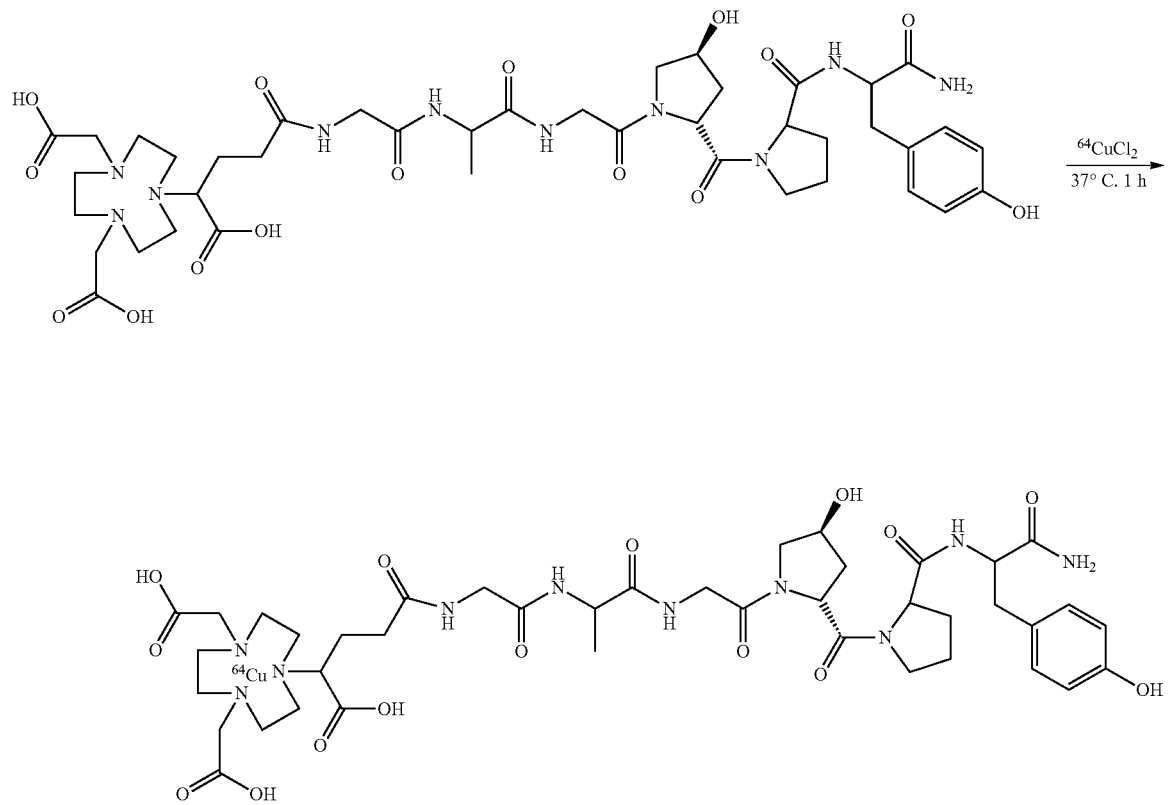

The Chemical Reaction Formula of Labeling NODA-Cx43SP1 with $^{64}$Cu

2) Labeling Cx43SP with $^{18}$F $^{18}$F is the most commonly used radionuclide clinically. It is very difficult to label a polypeptide with affinitive $^{18}$F-F$^-$ directly. Generally, modified $^{18}$F precursor such as 4-nitrophenyl 2-[$^{18}$F]-fluoropropionate ($^{18}$F-NFP) is used. By means of this technique, $^{18}$F labeled Cx43 probe suitable for Cx43 targeted molecular imaging of heart and tumor can be obtained. The probe is characterized by more clinical application potentials.

Synthesis of $^{18}$F-FP-Cx43SP:

$^{18}$F labeled precursor $^{18}$F-NFP (4-nitrophenyl 2-[$^{18}$F]-fluoropropionate, Rt=22-23 min) and 500 μg of Cx43 targeted binding peptide were dissolved in 150 μL of dry dimethyl sulfoxide (DMSO), and then $^{18}$F-NFP and 20 μL of N,N-diisopropyl ethylamine (DIPEA) were added. After the mixture was reacted at room temperature for 30 min, 800 μL of 5% acetic acid was added to neutralize. The product was purified with semi-preparative HPLC C-18 column. The purified product was diluted by adding 20 μL of water. During preparation, the C-18 column was repeatedly eluted with 5 mL of ethanol and 10 mL of water to elute products. The final product was blow-dried with nitrogen gas at 60° C. Finally, the $^{18}$F labeled polypeptide was dissolved in PBS and ultrafiltered (0.22 μm) into a sterile dose vial for in vitro and in vivo experiments. Likewise, the labeling rate, radiochemical purity, specific activity, etc. were tested by HPLC. The chemical reaction formula of labeling Cx43SP1 with $^{18}$F is as follows:

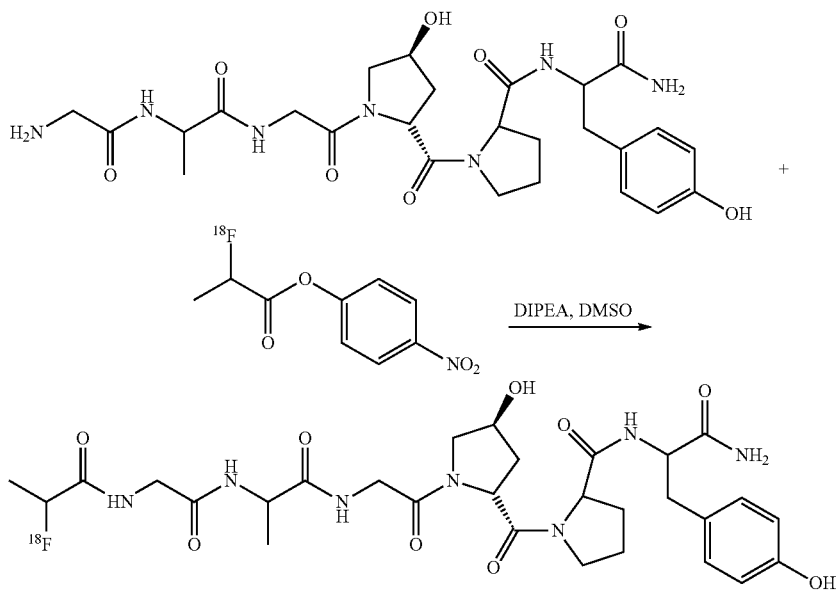

The Chemical Reaction Formula of Labeling Cx43SP1 with $^{18}$F

Synthesis of $^{18}$F-AlF-NODA-Cx43SP:

NODA-Cx43SP was synthesized by using NODA-Cx43SP. QMA-SepPak column was used to absorb 30 mCi (1.1 GBq) aluminum $^{18}$F-fluoride, 2.5 mL of aqueous solution without metal ions was used to elute aluminum $^{18}$F-fluoride, 400 μL of 0.4 M KHCO$_3$ solution was used to rinse aluminum $^{18}$F-fluoride, and 200 μL of aluminum $^{18}$F-fluoride solution was taken out for use. The pH of the solution was adjusted to 4.0 with acetic acid without metal ions. To the solution were sequentially added aluminium chloride (AlCl$_3$, 2mM, 3 μL, dissolved in 0.1 M sodium acetate buffer, pH 4) and 5 μL of NOTA-Cx43SP (60 mg/mL, dissolved in DMSO). The reaction mixture was incubated at 100° C. for 15 min, and diluted with 1 mL water without metal ions. The product was purified with semi-preparative HPLC. $^{18}$F-AlF-NOTA-Cx43SP analogs were collected and evaporated to dry, dissolved in PBS and ultrafiltered (0.22 μm) into a sterile dose vial for in vitro and in vivo experiments. Likewise, the labeling rate, radiochemical purity, specific activity, etc. were tested by HPLC. The chemical reaction formula of labeling Cx43SP1 with $^{18}$F is as follows.

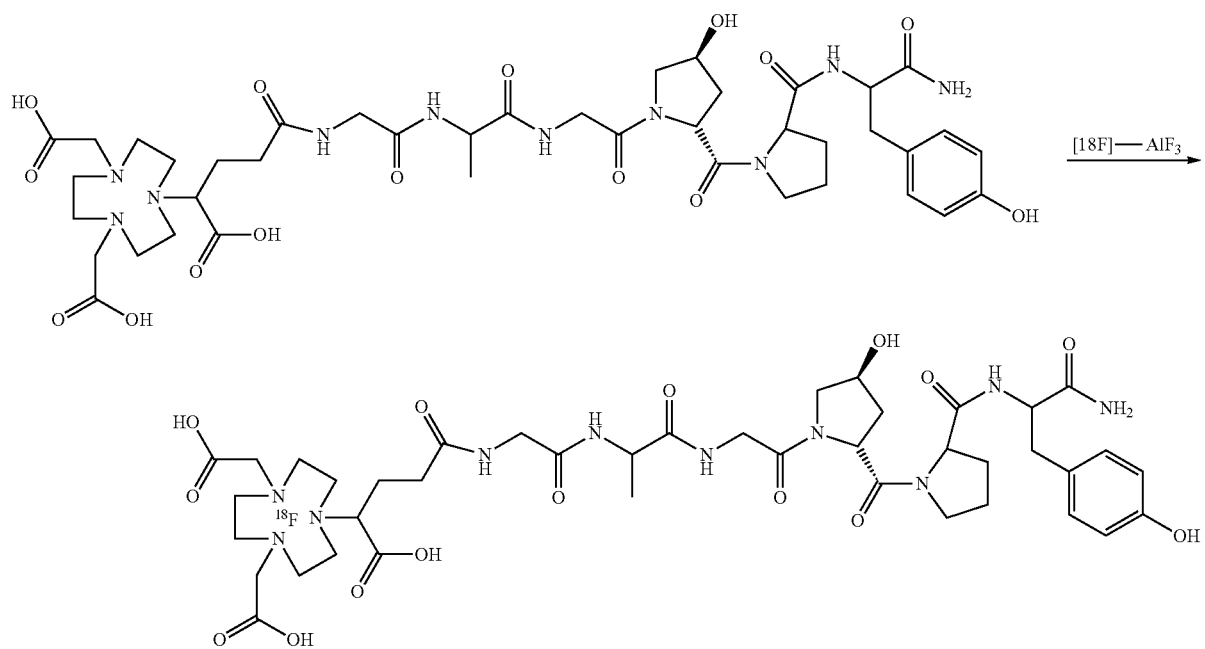

The Chemical Reaction Formula of Labeling Cx43SP1 with $^{18}$F

Besides $^{18}$F-NFP, similar processes may also be employed to label Cx43SP by means of other $^{18}$F precursors (i.e., auxiliary groups). Structural formulae of commonly used $^{18}$F labeled precursors [$^{18}$F] FBA: [$^{18}$F] o-fluorobenzoic acid; [$^{18}$F] FSB: [$^{18}$F] fluorobenzoate; [$^{18}$F] FBEM and [$^{18}$F] FBBO are as shown below:

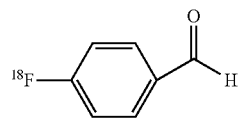

[$^{18}$F]FBA

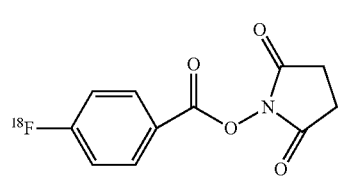

[$^{18}$F]FSB

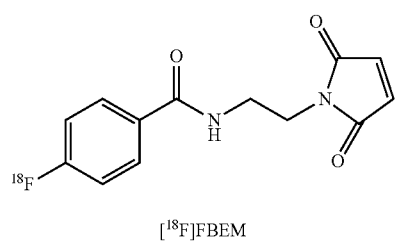

[$^{18}$F]FBEM

-continued

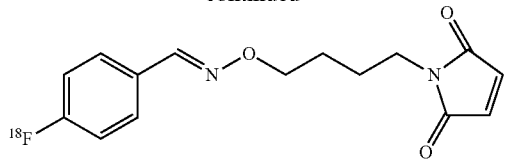

[$^{18}$F]FBBO

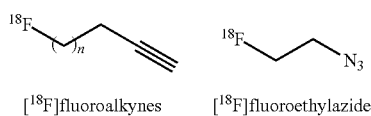

[$^{18}$F]fluoroalkynes    [$^{18}$F]fluoroethylazide

Besides $^{18}$F, Cx43SP may also be labeled by applying radionuclides such as $^{11}$C, $^{13}$N and $^{15}$O and selecting corresponding precursors. Advantages of positron emission radionuclide labeled probes include high sensibility, accurate quantification ability, clinical transformation ability, low molecular weight of probe, and good pharmacokinetic characteristics.

3): $^{99m}$Tc labeled Cx43SP

For Example: $^{99m}$TcO$^{3+}$ or $^{99m}$TcO$^{2+}$, with HYNIC as a Bifunctional Chelating Agent.

Specific steps are as follows:

1. The bifunctional chelating agent HYNIC-NHS was reacted with amino (—NH$_2$) on Cx43SP, with DMF as solvent, 2% of DIPEA as catalyst. After purification by high pressure liquid chromatography (HPLC), the product was identified by mass spectrometry.

2. Technetium-99m labeled HYNIC-Cx43SP: by means of a protocol of complexation with "3+1" binary mixed ligands, in which a tridentate ligand tricine was used as a synergistic reagent, and stannous chloride ($SnCl_2 \cdot H_2O$) was used as a reducing agent. After reaction at room temperature for 20 min, radiochemical purity of the labeled compound was tested, and the casted colloid was less than 1%.

3. Analysis: Thin Layer Chromatography (ITLC) and high pressure liquid chromatography (HPLC) were used to analyze the content of colloid in the labeled compound and content of product.

The chemical reaction formula of labeling Cx43SP1 with $^{99m}Tc$ is as follows:

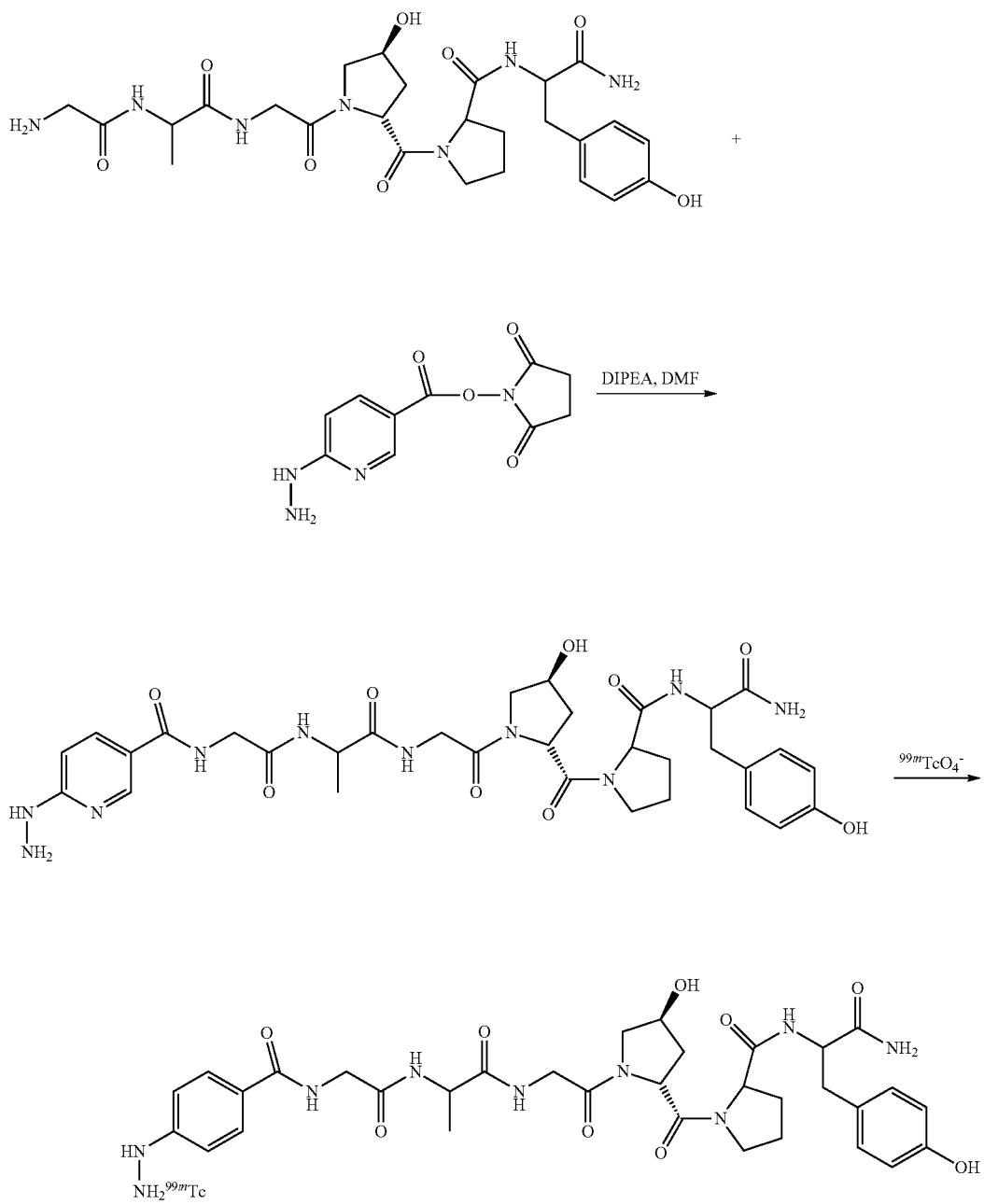

The Chemical Reaction Formula of Labeling Cx43SP1 with $^{99m}Tc$

Different products can be obtained depending on different $^{99m}Tc$-nuclei, different linkers, and different reaction processes. $^{99m}Tc$ labeled Cx43SP, common bifunctional chelating agents and synthesized probes are as shown in Table 2, wherein R represents Cx43SP:

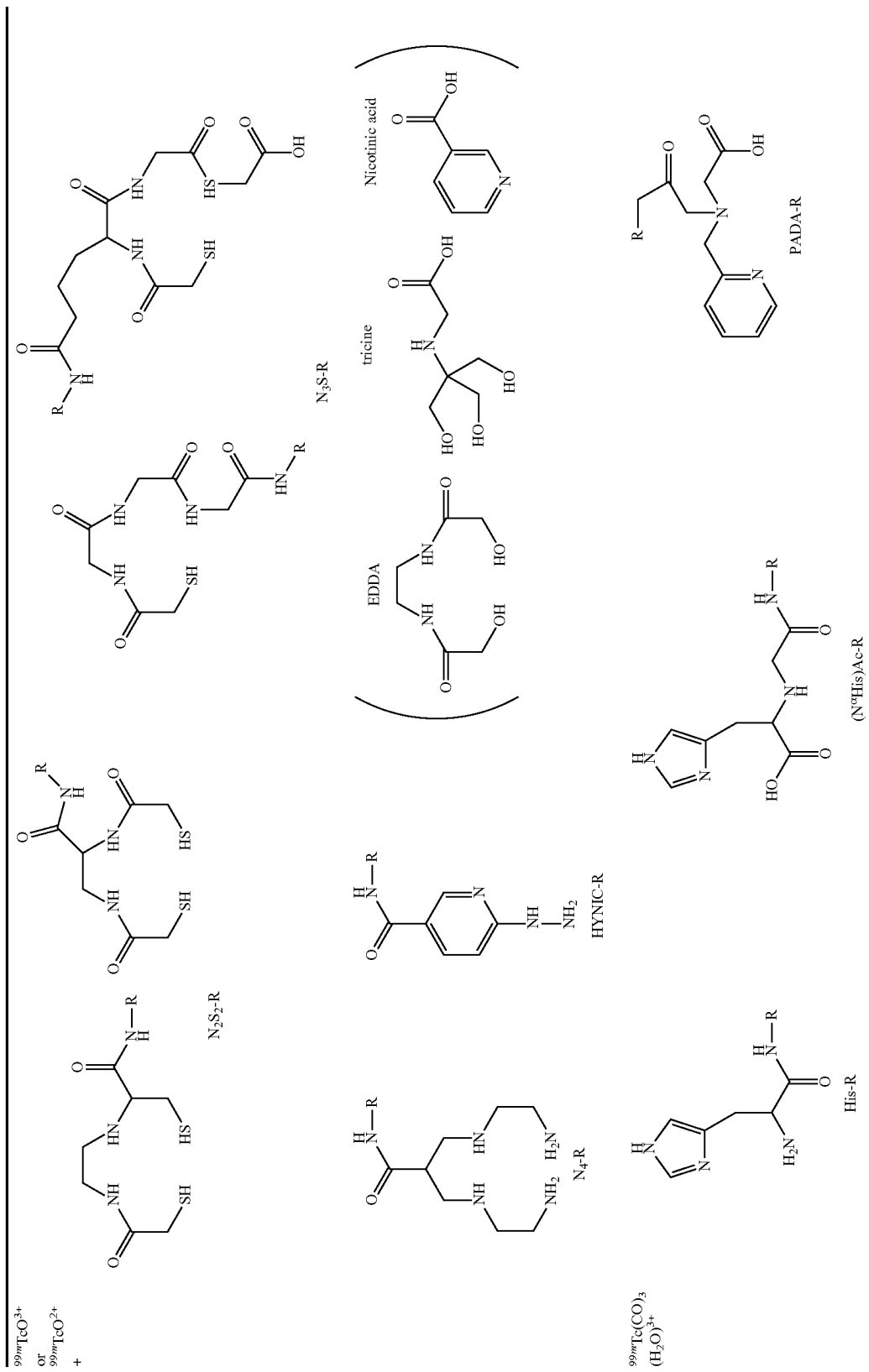

4) $^{123/124}$I labeled Cx43SP

Radioisotope iodine can be labeled on Cx43SP by selecting appropriate oxidants. There are mainly 2 types of labeling methods, i.e., direct labeling and indirect labeling.

(1) Direct labeling: iodination reaction may be directly carried out via "iodine protonation". Structural formulae of oxidants commonly used in direct labeling of Cx43SP with $^{123/124}$I are as follows:

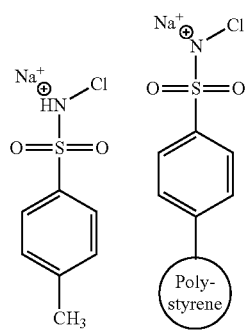

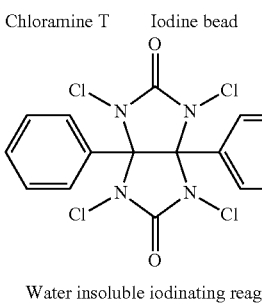

Chloramine T   Iodine bead   Water insoluble iodinating reagent

The chemical reaction formula of direct labeling Cx43SP1 with $^{123/124}$I is as follows:

(2) Indirect labeling: Structural formulae of oxidants commonly used in indirect labeling of Cx43SP with $^{123/124}$I are as follows:

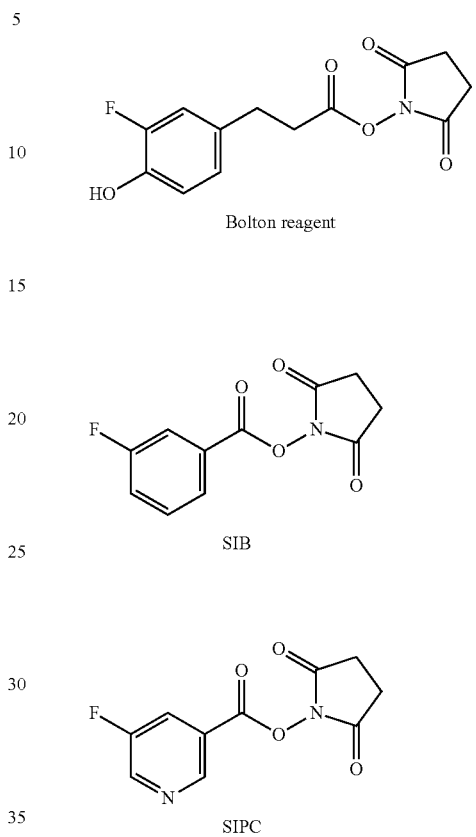

The chemical reaction formula of indirect labeling Cx43SP1 with $^{123/124}$I is as follows:

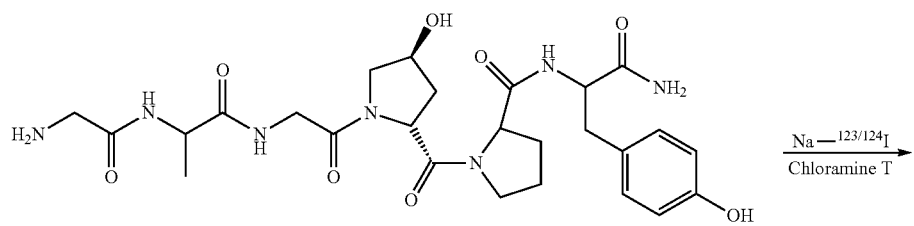

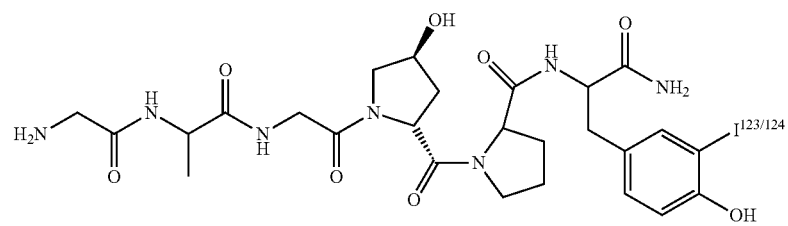

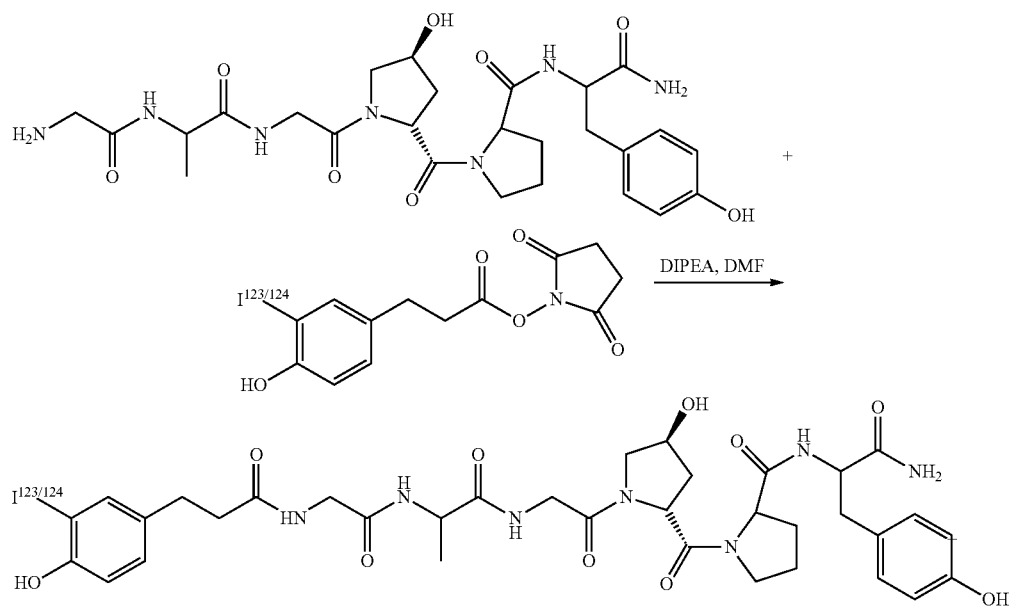

EXAMPLE 4

Preparation of Optically Labeled Cx43 Targeted Molecular Probe

1) Near-infrared fluorescent dye labeled Cx43SP1

Near-infrared fluorescent dyes at a wavelength of 700-900 nm can reach deeper tissues due to their stronger penetration, and therefore often are used to carry out in vivo optical imaging. Commonly used near-infrared fluorescent dyes are shown in figures. Different bifunctional chelating agents can be selected to label a near-infrared fluorescent dye onto Cx43SP. The chemical structural general formula of cyanine dye is as follows:

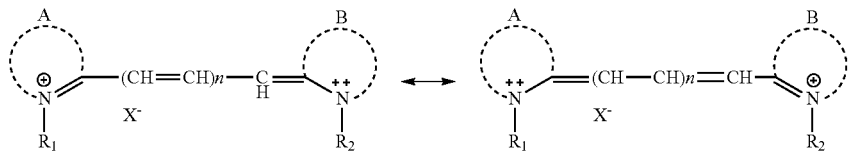

The chemical structures of commonly used 4 types of near-infrared fluorescent dyes are as follows:
(1a) cyanine, (1b) ICG, (1c) SIDAG, (1d) PPCy Chemical structural general formulae of the cyanine dye

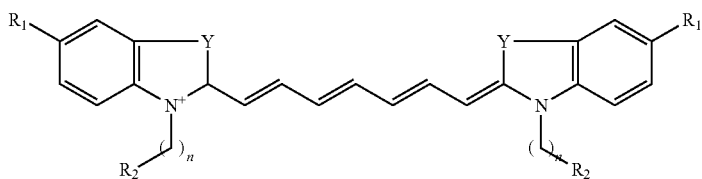

1a

-continued

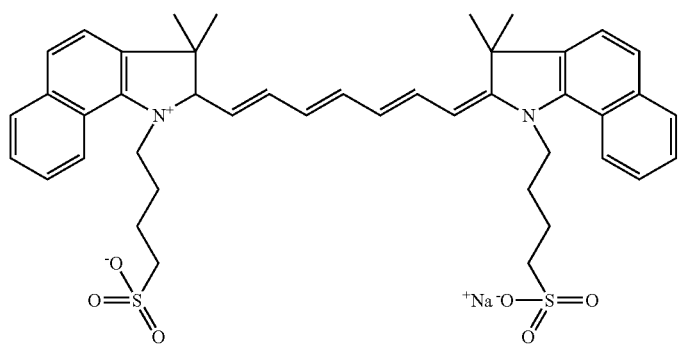
1b

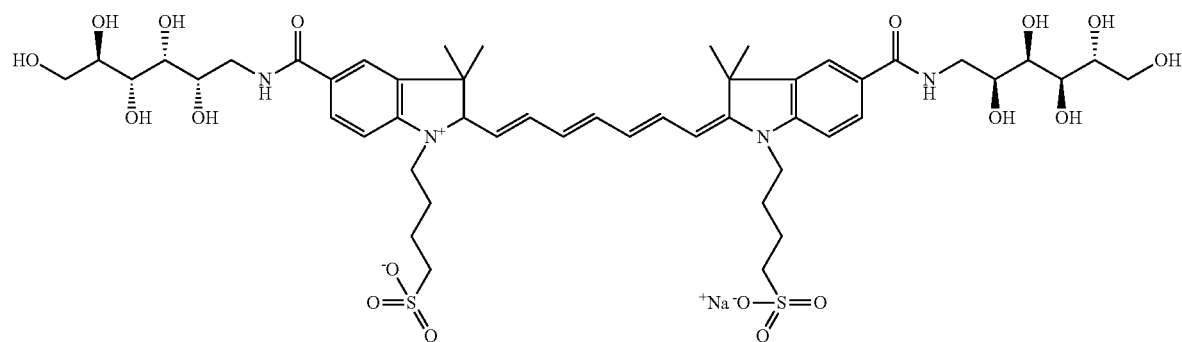
1c

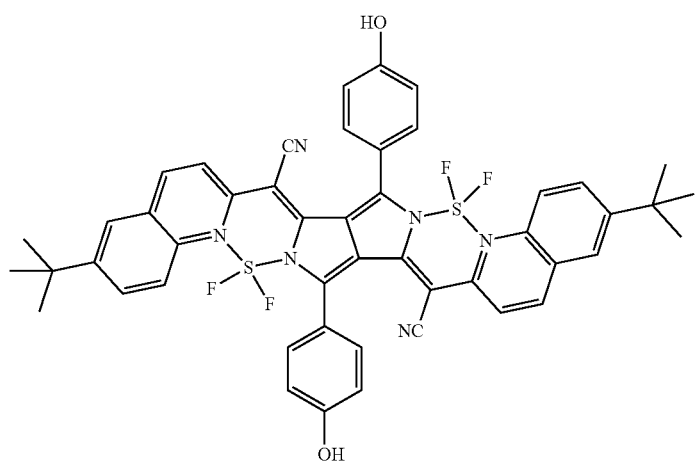
1d

Chemical structural general formulae of the cyanine dye

Cy5.5 labeling: Cx43-specific binding peptide dissolved in 100 μL of DMSO was mixed with Cy5.5-NHS (1 equiv.) under light screening condition, co-dissolved in 2% DIPEA, and incubated under vibration overnight at room temperature. The product was isolated and purified via semi-preparative HPLC C18 column (250×10 mm), then collected and lyophilized. The yield of the product was calculated, and molecular weight thereof was measured by mass spectrometry (MALDI-TOF-MS). The chemical reaction formula of labeling Cx43SP1 with Cy5.5 is as follows:

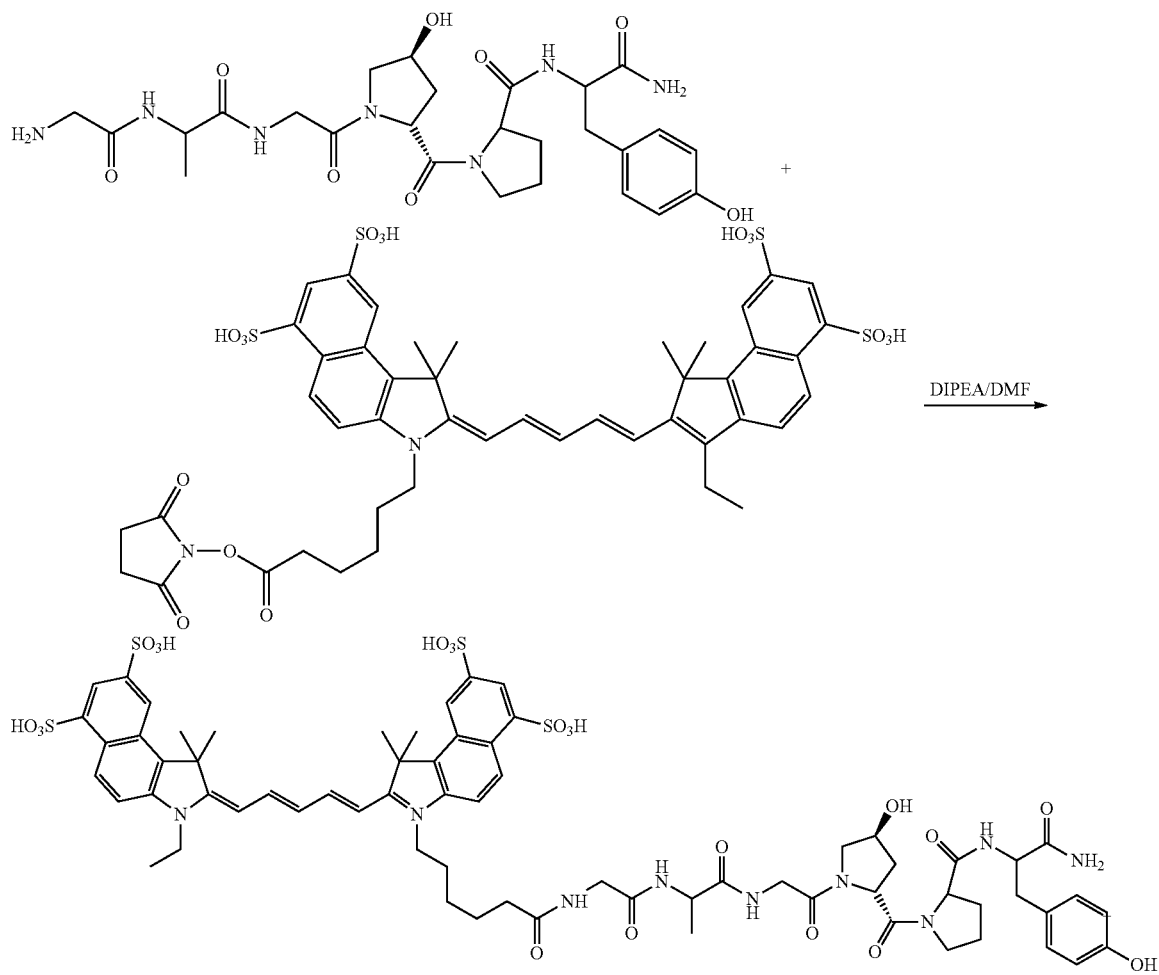

2) Near-infrared nano material labeled Cx43SP

There are four types of most commonly used nano materials at present, including nano probe, quantum dot, carbon nano tube and gold nanocluster containing a near-infrared fluorescent dye.

Taking near-infrared quantum dot as an example, quantum dot was used to label Cx43SP: 1000 eq of Cx43SP was dissolved in water, mixed with 1 eq of quantum dot. 1000 eq of EDC was then added. The reaction mixture was stirred at room temperature for 1 hour, then isolated on PD10 column, concentrated via a centrifuge tube, and tested for concentration. One quantum dot can be labeled with 500-600 Cx43SP molecules. The synthesized probe was subjected to in vivo test via near-infrared fluorescent imaging.

EXAMPLE 5

Preparation of a Magnetically Labeled Cx43 Targeted Molecular Probe

1) Superparamagnetic nanoparticles ($Fe_3O_4$)

Superparamagnetic nanoparticles were used to label Cx43SP to synthesize the probe useful in magnetic resonance imaging. Taking superparamagnetic nanoparticles as an example, using superparamagnetic nanoparticles to label Cx43SP: 1000 eq Cx43SP was dissolved in water and mixed with 1 eq superparamagnetic nanoparticles. 1000 eq of EDC was then added. The reaction mixture was stirred at room temperature for 1 hour, then isolated on PD10 column, concentrated via a centrifuge tube, and tested for concentration. The chemical reaction formula of labeling Cx43SP1 with superparamagnetic ferric oxide is as follows:

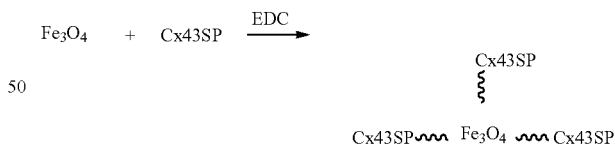

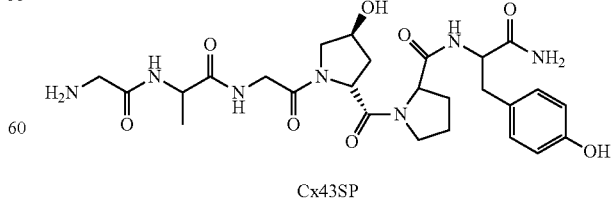

2) Paramagnetic metal chelate: through selecting proper bifunctional chelating agent, a paramagnetic metal chelate can also be labeled on Cx43SP to form a probe useful in magnetic resonance imaging. The paramagnetic metal element mainly include gadolinium ($Gd^{3+}$), $Dy^{3+}$, $Tm^{3+}$, $Mn^{2+}$, CEST reagent, $^3He$, and $^{129}Xe$. Due to the relatively week ability of relaxation generated by the paramagnetic metal chelate, whereas the sensibility of magnetic resonance molecular imaging is relatively low, effective signal magnification mechanism may also be introduced, i.e., by using macromolecules carrying multiple functional groups on the surface, such as dendrimer, liposome, etc., several Cx43SP molecules and plenty of paramagnetic metal were chelated onto their surfaces to form a probe. The chemical reaction formula of labeling Cx43SP1 with a paramagnetic metal chelate is as follows:

EXAMPLE 6

Preparation of Ultrasound Microbubble Labeled Cx43 Targeted molecular probe 1000 eq Cx43SP was dissolved in water, and mixed with 1 eq ultrasound microbubble. 1000 eq EDC was then added. The reaction mixture was stirred at room temperature for 1 hour. The chemical reaction formula of labeling Cx43SP1 with ultrasound microbubble is as follows:

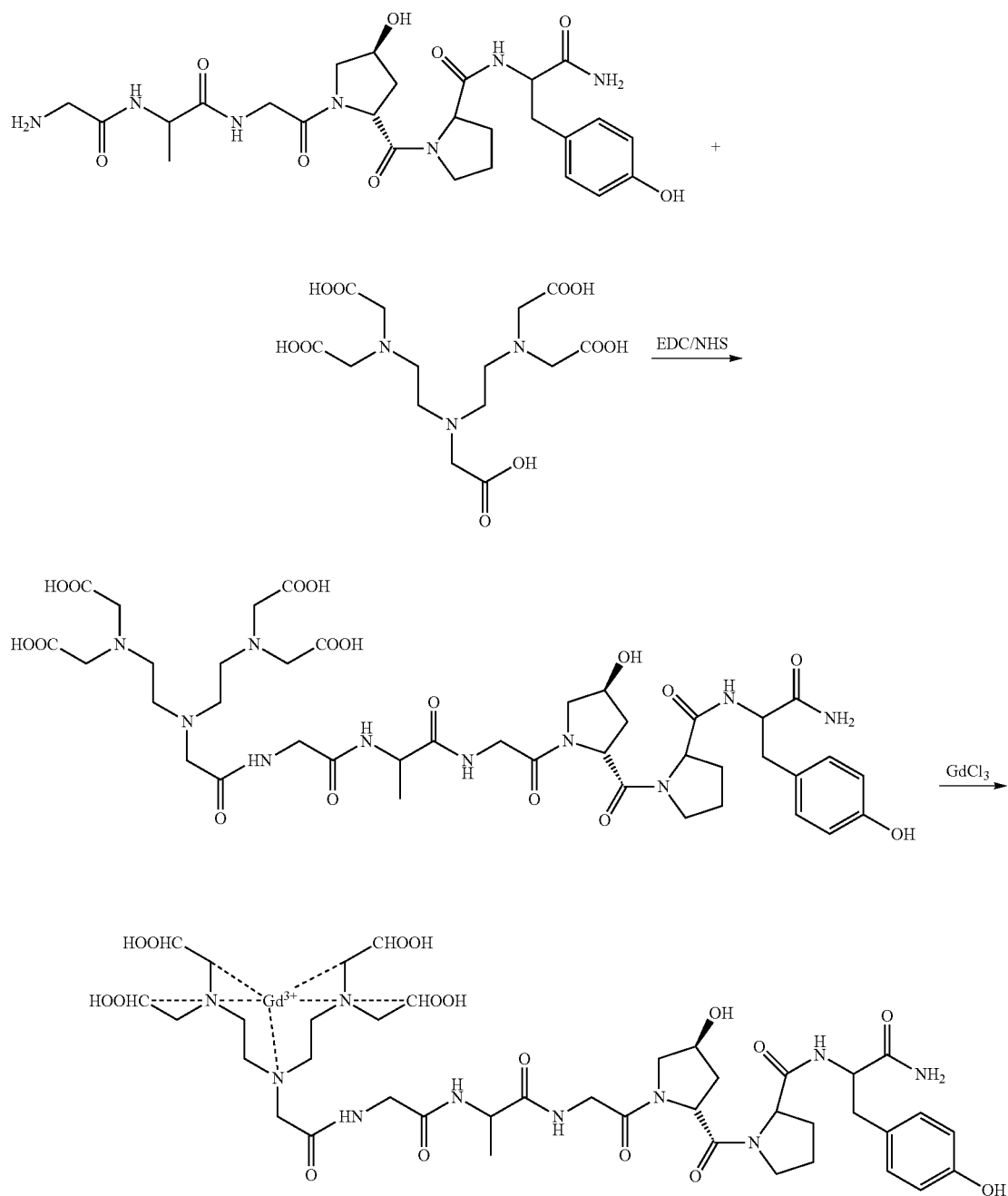

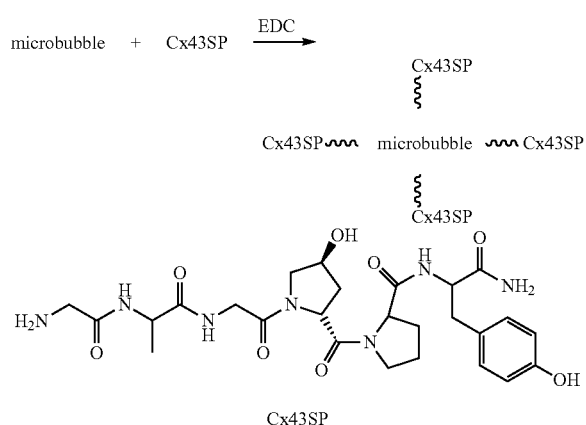

EXAMPLE 7

Preparation of Photoacoustic Material Labeled Cx43 Targeted Molecular Probe

At present, some gold nanoparticles, such as gold nanorod, can also be used to label Cx43SP to perform photoacoustic imaging. Using gold nanorod to labelCx43SP: 1000 eq Cx43SP was dissolved in water and mixed with 1 eq gold nanorod. 1000 eq EDC was then added. The reaction mixture was stirred at room temperature for 1 hour, then isolated on PD10 column, concentrated via a centrifuge tube, and tested for concentration. The chemical reaction formula of labeling Cx43SP1 with gold nanorod is as follows:

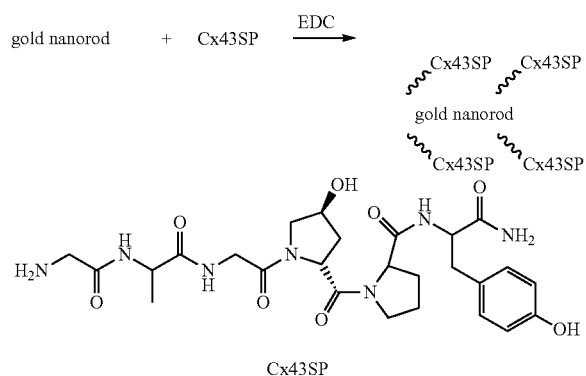

EXAMPLE 8

Preparation of a Multi-mode Labeled Cx43 Targeted Molecular Probe

Two or more types of imaging labeling processes were simultaneously used to generate a Cx43 targeted probe detectable via two or more of imaging detection means, i.e., a multi-mode molecular imaging probe. For example, different functional groups were attached to the surface of a nano material, in order to attach other modes of imaging agents such as polypeptide, radionuclide, fluorescent dye, etc.

After modification with mercapto and carboxyl groups on the surface of near-infrared quantum dots, Cx43SP1 was firstly attached thereto. Quantum dots were modified with NODA-MAL. By means of the reaction between maleic anhydride and mercapto, NODA was attached to the quantum dots. Then the product was labeled with $^{64}$Cu. The radiolabeled product was isolated and purified via PD10. The labeling rate, radiochemical purity, and specific activity were tested. The probe can be used simultaneously for near-infrared fluorescent imaging and PET imaging. The chemical reaction formula of double-mode labeling Cx43SP1 with $^{64}$Cu and quantum dots is as follows:

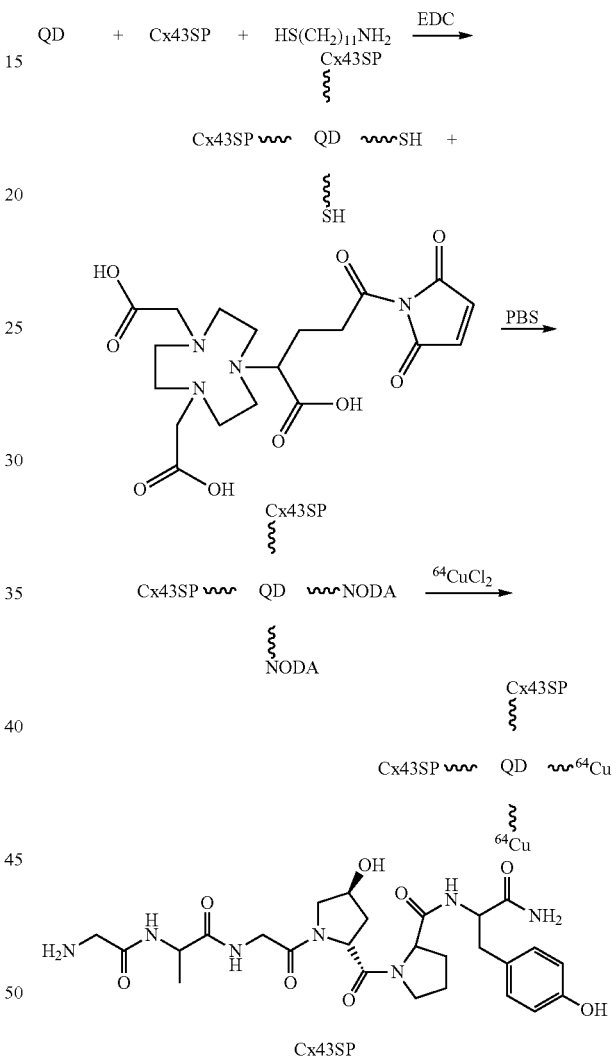

EXAMPLE 9

Ex Vivo Experiment Verification

1) Establishment of a Cx43 highly expressing cell line: Cervical cancer HeLa cells were transfected by Cx43 gene, and cervical cancer tumor cell lines HeLa-Cx43 overexpressing Cx43 was successfully prepared. Non-transgenic HeLa cells (without C43 expression) were used as control.

2) Cy5.5-Cx43SP1 cells binding and blocking experiment: HeLa-Cx43 cells and the control group HeLa-Control cells were applied onto a 12-well plate in an amount of 0.5×10⁶/well one day prior to experiment, and were classified into four groups: Group A: HeLa-Cx43 cells group, Group B: HeLa-Control cells group, Group C: HeLa-Cx43 cells blocking group, Group D: HeLa-Control cells blocking group. Each group comprises 3 wells and the experiment was repeated for 3 times. Into each well was added Cy5.5-Cx43SP1 with a concentration of 500 nmol/L and an amount of 1 ml. Unlabeled Cx43SP1 was added into blocking groups with a concentration of 5 µmol/L.

Figure 2:
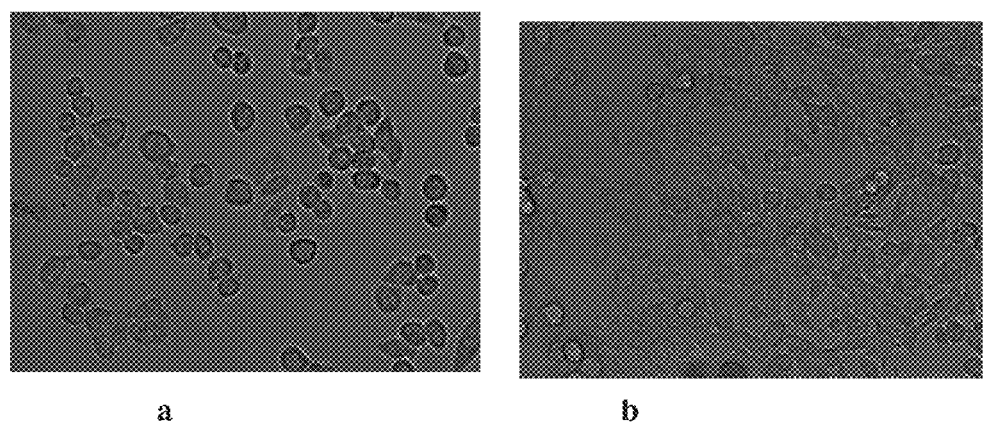
FIG. 2 shows fluorescent micrographs of an experiment showing the binding of the probe with HeLa-Cx43 cells in vitro.

As can be seen from the results, there was significant specific binding between Cy5.5-Cx43SP1 and HeLa-Cx43 cells, and no binding between Cy5.5-Cx43SP1 and the control group HeLa cells without transfecting Cx43 gene (FIG. 2-a and FIG. 2-b). After blocking by introduction of an excess of unlabeled 5 µmol/L Cx43SP, the binding between Cy5.5-Cx43SP and HeLa-Cx43 was substantially reduced (FIG. 2-c). The above results show that, the near-infrared fluorescent probe Cy5.5-Cx43SP can be specifically uptaken by HeLa cells overexpressing Cx43, and the binding between Cy5.5-Cx43SP and HeLa-Cx43 has target specificity.

Meanwhile, frozen sections of tissue were further prepared and imaged under a fluorescence microscope. By using muscle as a control (FIGS. 3-a, 3-b, and 3-c), the distribution profile of the probe Cy5.5-Cx43SP in heart was observed under a fluorescence microscope. At 1 h after tail vein injection of Cy5.5-Cx43SP, frozen myocardium sections showed under a fluorescence microscope that Cy5.5-Cx43SP was gathered in the myocardial tissue in large amount, and was mainly distributed at the location of gap junctions between myocardial cells (FIGS. 4-a, 4-b, and 4-c). It is proved at tissue level that the probe has target specificity to the myocardial gap junctions.

3) $^{64}$Cu-NODA-Cx43SP1 Cells Binding and Blocking Experiment

HeLa-Cx43 cells and control group HeLa-Control cells were applied onto a 12-well plate in an amount of 0.5×10⁶/well one day prior to experiment, and were classified into four groups: Group A: HeLa-Cx43 cells group, Group B: HeLa-Control cells group, Group C: HeLa-Cx43 cells blocking group, Group D: HeLa-Control cells blocking group. Each group comprises 3 wells, and the experiment was repeated for 3 times. Into each well was added $^{64}$Cu-NODA-Cx43SP1 with a concentration of 3.2 µCi/well and an amount of 1 ml. Unlabeled NODA-Cx43SP1 was added into the blocking groups with a concentration of 50 µg/well (10 times of $^{64}$Cu-NODA-Cx43SP1). The results show that, there was significant specific binding between $^{64}$Cu-NODA-Cx43SP1 and HeLa-Cx43 cells, and no binding between $^{64}$Cu-NODA-Cx43SP1 and the control group HeLa cells without transfecting Cx43 gene. In the blocking experiment, the binding between $^{64}$Cu-NODA-Cx43SP1 and HeLa-Cx43 was substantially reduced (FIG. 5). The results show that, -NODA-Cx43SP1 can be specifically uptaken by HeLa cells overexpressing Cx43, and the binding between -NODA-Cx43SP1 and HeLa-Cx43 has target specificity and high affinity.

EXAMPLE 10

Animal Experiments

1) In Vivo Biological Distribution Characteristics of the Probe:

Biological Distribution of Cy5.5-Cx43SP in Normal Mice 1 hour after injection of Cy5.5-Cx43SP, the mice were sacrificed, and their organs were taken out to perform ex vivo near-infrared fluorescent imaging of main organs. The results show that, the probe Cy5.5-Cx43SP was mainly distributed in heart, liver, gastrointestinal tract, and was mainly excreted through liver and intestinal tract, and partly through kidney and urinary system. Especially, the relatively high uptake by heart is highly consistent with the fact that normal heart express relatively high Cx43 (FIG. 6).

2) Normal Rat PET Heart Imaging:

The previous experiment verified at in vivo level the target gathering ability of $^{64}$Cu-NOTA-Cx43SP in the heart of a normal rat and the biological distribution characteristics of the probe. The results show that, at 30 min after intravenous injection of $^{64}$Cu-NOTA-Cx43SP, it began to gather in the heart significantly, and some of the probe maintained in the heart until 3 h after the injection (FIG. 7), while the probe seldom gather in liver and lung, as the images of the myocardium were clear. Since Cx43 is the main connexin in the myocardium, the results show that $^{64}$Cu-NOTA-Cx43SP was target gathered in the myocardium. At 1 h after the intravenous injection, the probe $^{64}$Cu-NOTA-Cx43SP was mainly distributed in heart and intestinal tract of mice. These results are consistent to the in vitro optical imaging results of Cy5.5-Cx43SP in mice. The experimental results demonstrate that Cx43 targeted molecular probe $^{64}$Cu-NOTA-Cx43S designed in the preliminary experiment can be used in in vivo imaging of the myocardium.

3) PET Heart Imaging of Normal Mice:

PET imaging experiment of $^{64}$Cu-NOTA-Cx43SP in normal mice was simultaneously carried out. The results are shown in FIG. 8. At 1 h after intravenous injection of $^{64}$Cu-NOTA-Cx43SP, it was significantly gathered in heart, and was also absorbed in liver. Most of $^{64}$Cu-NOTA-Cx43SP was excreted through kidney and urinary bladder. These results are consistent with the rat experiment, but not so good as the heart imaging results in rats. It shows that biological distributions of the probe in different animals are somewhat different. Meanwhile, the $^{64}$Cu-NOTA-Cx43SP probe can be further optimized and need to be further optimized.

4) Optical Tumor Imaging of Nude Mice Bearing Tumor:

HeLa-Cx43 cells overexpressing Cx43 were used to establish a subcutaneous xenograft model in nude mouse (FIG. 9, left), and the conventional subcutaneous xenograft model of HeLa cells without transfection of Cx43 were used as control group (FIG. 9, right). In vivo Cy5.5-Cx43SP1 near-infrared fluorescent imaging of tumor was carried out. The results show that, at one hour after tail vein injection of the probe Cy5.5-Cx43SP1, it was gathered in the location of HeLa-Cx43 tumor overexpressing Cx43 in high concentration, and no obvious gather in the location of HeLa tumor in the control group was observed. The results once again show that, at in vivo level, Cx43 targeted molecular probe Cy5.5-Cx43S has certain degree of target specificity to Cx43 positive tumor.

5) PET Tumor Imaging of Nude Mice Bearing Tumor:

HeLa-Cx43 cells overexpressing Cx43 were used to establish a subcutaneous xenograft model in nude mouse (FIG. 10, left). $^{64}$Cu-NODA-Cx43SP was intravenously injected, with a concentration of 40 microcurie. The results of Micro PET imaging show that, at one hour after tail vein injection of the probe $^{64}$Cu-NODA-Cx43SP, it was gathered in the location of HeLa-Cx43 tumor overexpressing Cx43 in high concentration. The results once again show that, at in vivo level, Cx43 targeted molecular probe $^{64}$Cu-NODA-Cx43SP has certain degree of target specificity to Cx43 positive tumor.

The invention claimed is:

1. A process for in vivo molecular imaging, comprising:
providing a Cx43 targeted molecular probe consisting of three components: a signaling component, a Cx43 targeted affinity component and a linker, wherein the signaling component is a moiety which is detectable by an imaging device, the Cx43 targeted affinity component is a polypeptide moiety which specifically binds to Cx43, and the linker links the signaling component to the targeted affinity component;
carrying out optical imaging, positron emission tomography (PET), single photon emission tomography, magnetic resonance imaging, photoacoustic imaging, or ultrasonic imaging the site to be detected in a patient by using the Cx43 targeted molecular probe;
wherein the Cx43 targeted affinity component specifically binds to the carboxyl terminal of Cx43, and the targeted affinity component is Cx43SP1, Gly-Ala-Pro-Gly-4 Hyp-Pro-Tyr.

2. The process according to claim 1, characterized in that the signaling component of the Cx43 targeted probe is one or more selected from the group consisting of radioisotope, fluorescent dye, quantum dot, paramagnetic material, magnetic nanoparticle, super-paramagnetic material, ultrasound microbubble, and photoacoustic nanoparticle.

3. The process according to claim 1, characterized in that the linker is a chelating agent selected from the group consisting of DTPA, DOTA, DOTAGA, NOTA, NODAGA, TETA, CB-TE2A, Sar, and NODA, or a direct chemical reaction is used to directly link the signaling component to the Cx43 affinity component.

4. A Cx43 targeted molecular probe consisting of three components: a signaling component, a Cx43 targeted affinity component and a linker linking the signaling component to the targeted affinity component, wherein the signaling component is a moiety which is detectable by an imaging device, the targeted affinity component is a moiety which specifically binds to Cx43, and the linker links the signaling component to the targeted affinity component, wherein the targeted affinity component specifically binds to the carboxyl terminal of Cx43, and the targeted affinity component is Cx43SP1, Gly-Ala-Pro-Gly-4 Hyp-Pro-Tyr.

5. The targeted molecular probe according to claim 4, characterized in that the signaling component is one or more selected from the group consisting of radioisotope, fluorescent dye, quantum dot, paramagnetic material, magnetic nanoparticle, super-paramagnetic material, ultrasound microbubble, and photoacoustic nanoparticle.

6. The targeted molecular probe of claim 4, characterized in that, the linker is a chelating agent selected from the group consisting of DTPA, DOTA, DOTAGA, NOTA, NODAGA, TETA, CB-TE2A, Sar, and NODA, or a direct chemical reaction is used to directly link the signaling component to the Cx43 affinity component.

7. A method for diagnosing a disease associated with abnormal Cx43 expression in a subject, comprising administering the targeted molecular probe of claim 4 to the subject, wherein the disease is a tumor or a cardiovascular disease.

8. The method according to claim 7, wherein the cardiovascular disease is myocardial ischemia, arrhythmia, cardiac failure, hypertension and atherosclerosis.

9. The method according to claim 7, wherein the disease associated with abnormal Cx43 expression is a tumor.

10. The process of claim 1 wherein PET is selected from PET/CT and PET/MRI.

* * * * *

UNITED STATES PATENT AND TRADEMARK OFFICE
CERTIFICATE OF CORRECTION

PATENT NO. : 9,764,048 B2
APPLICATION NO. : 14/353111
DATED : September 19, 2017
INVENTOR(S) : Baozhong Shen, Zhen Cheng and Lihong Bu Page 1 of 1

It is certified that error appears in the above-identified patent and that said Letters Patent is hereby corrected as shown below:

In Claim 1, Column 49, Line 31, after "ultrasonic imaging", insert --to--.

Signed and Sealed this
Seventh Day of November, 2017

Joseph Matal
*Performing the Functions and Duties of the
Under Secretary of Commerce for Intellectual Property and
Director of the United States Patent and Trademark Office*